(12) United States Patent
Mumper et al.

(10) Patent No.: US 8,367,126 B2
(45) Date of Patent: Feb. 5, 2013

(54) BERRY PREPARATIONS AND EXTRACTS

(75) Inventors: Russell J. Mumper, Chapel Hill, NC (US); Jin Dai, Lexington, KY (US); Vincent S. Gallicchio, Belton, SC (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/157,531

(22) Filed: Jun. 10, 2011

(65) Prior Publication Data
US 2011/0244038 A1 Oct. 6, 2011

Related U.S. Application Data

(63) Continuation-in-part of application No. 12/088,156, filed as application No. PCT/US2006/037237 on Sep. 26, 2006, now Pat. No. 7,964,233.

(60) Provisional application No. 60/720,892, filed on Sep. 27, 2005.

(51) Int. Cl.
*A61K 36/00* (2006.01)
*A61K 36/45* (2006.01)

(52) U.S. Cl. .................. 424/725; 424/732; 424/777

(58) Field of Classification Search .................. None
See application file for complete search history.

(56) References Cited

U.S. PATENT DOCUMENTS

| | | |
|---|---|---|
| 4,933,177 A | 6/1990 | Grollier et al. |
| 5,750,134 A | 5/1998 | Scholz et al. |
| 5,750,149 A | 5/1998 | Gobbi |
| 6,383,546 B1 | 5/2002 | Powrie et al. |
| 6,576,271 B2 | 6/2003 | Nair et al. |
| 6,608,108 B2 | 8/2003 | Huang et al. |
| 6,623,743 B1 | 9/2003 | Nair et al. |
| 6,656,914 B2 | 12/2003 | Nair et al. |
| 6,676,978 B1 | 1/2004 | Nair |
| 6,756,051 B1 | 6/2004 | Chen et al. |
| 6,783,754 B2 | 8/2004 | Mankovitz |
| 6,818,234 B1 | 11/2004 | Nair et al. |
| 2001/0016573 A1 | 8/2001 | Nair et al. |
| 2002/0102336 A1* | 8/2002 | Mann .................. 426/321 |
| 2003/0091660 A1 | 5/2003 | Slimestad |
| 2003/0194435 A1 | 10/2003 | Mercati |
| 2004/0106175 A1 | 6/2004 | Noel et al. |
| 2004/0109905 A1 | 6/2004 | Bagchi |
| 2004/0132672 A1 | 7/2004 | Nair et al. |
| 2004/0137094 A1 | 7/2004 | Mower et al. |
| 2004/0161523 A1 | 8/2004 | Nair et al. |
| 2005/0013880 A1* | 1/2005 | Magnuson et al. ........ 424/732 |
| 2005/0037130 A1 | 2/2005 | Nair et al. |
| 2005/0100622 A1 | 5/2005 | Nair et al. |
| 2005/0136141 A1 | 6/2005 | Stoner et al. |
| 2005/0152997 A1 | 7/2005 | Selzer et al. |
| 2005/0244375 A1 | 11/2005 | Leonard et al. |
| 2005/0281772 A1 | 12/2005 | Bromley et al. |
| 2010/0047371 A1 | 2/2010 | Mumper |

FOREIGN PATENT DOCUMENTS

| | | |
|---|---|---|
| JP | 10075995 A | 3/1998 |
| JP | 2000/176272 | 6/2000 |
| WO | WO 02/17732 A2 * | 3/2002 |
| WO | WO 2003/074067 | 2/2003 |
| WO | WO 2004/026325 | 9/2003 |
| WO | WO 2005/000330 | 1/2005 |

OTHER PUBLICATIONS

Xie et al, Improvement of physicochemical and nutritional qualities of frozen Marionberry by vacuum impregnation pretreatment with cryoprotectants and minerals. Journal of Horticultural Science and Biotechnology (2003) vol. 78, No. 2, pp. 248-253.*
Laura A. Kretsy, et al., "Chemoprevention of Esophogeal Tumorigenesis by Dietary Administration of Lyophilized Black Raspberries," Cancer Research 61, 6112 6119, Aug. 15, 2001.
Gary D. Stoner, et al., "Pharmacokinestics of Anthocyanins and Ellagic Acid in Healthy Volunteers Fed 45 g of Freeze-Dried Black Raspberries Daily for 7 Days," Clin Pharmacol 2005; 45:1-12.
Bruce C. Casto, et al., "Chemoprevention of Oral Cancer by Black Raspberries," Anticancer Research 22:4005-4016 (2002).
Matt Ernst, "Business in Brambles," Business Lexington, Jul. 29, 2005, vol. 1 Issue 7, 4 pages.
Jim Warren, "Raspberry gel might help prevent cancer," Lexington Herald-Leader, Section C, Saturday, Apr. 9, 2005, 2 pages.
Chang, Y.C., et al., Hibiscus anthocyanins rich extract-induced apoptotic cell death in human promyelocytic leukemia cells. Toxicol Appl Pharmacol, 2005. 205(3): p. 201-12.
Dugo, P., et al., Identification of anthocyanins in berries by narrow-bore high-performance liquid chromatography with electrospray ionization detection. J Agric Food Chem, 2001. 49(8): p. 3987-3992.
Giusti, M.M. and R.E. Wrolstad, Characterization and measurement of anthocyanins by UV-visible spectroscopy., in Current Protocols in Food Analytical Chemistry, R.E. Wrolstad, et al., Editors. 2001, John Wiley & Sons: NY. p. F1.2.1-F1.2.13.
Hakimuddin, F., G. Paliyath, and K. Meckling, Selective cytotoxicity of a red grape wine flavonoid fraction against MCF-7 cells. Breast Cancer Res Treat, 2004. 85(1): p. 65-79.
Hecht, S.S., et al., Identification of cyanidin glycosides as constituents of freeze-dried black raspberries which inhibit anti-benzo[a]pyrene-7,8-diol-9,10-epoxide induced NFkappaB and AP-1 activity. Carcinogenesis, 2006. 27(8): p. 1617-26.
Hertog, M.G., et al., Intake of potentially anticarcinogenic flavonoids arid their determinants in adults in The Netherlands. Nutr Cancer, 1993. 20(1): p. 21-9.
Hou, D.X., et al., Anthocyanidins inhibit cyclooxygenase-2 expression in LPS-evoked macrophages: structure-activity relationship and molecular mechanisms involved. Biochem Pharmacol, 2005. 70(3): p. 417-25.

(Continued)

*Primary Examiner* — Qiuwen Mi
(74) *Attorney, Agent, or Firm* — King & Schickli, PLLC

(57) ABSTRACT

Compositions having antioxidant and anti-inflammatory activity, and methods for providing such compositions, are disclosed. In one aspect, the compositions are derived by exposing a berry to an acidic solvent composition, adding a cryoprotectant, and recovering a berry extract having a stabilized anthocyanin content. Compositions comprising the stabilized anthocyanin-containing berry extract, formulated for oral and/or topical administration, are provided also.

29 Claims, 9 Drawing Sheets

OTHER PUBLICATIONS

Hu, C., et al., Black rice (*Oryza sativa* L. indica) pigmented fraction suppresses both reactive oxygen species and nitric oxide in chemical and biological model systems. J Agric Food Chem, 2003. 51(18): p. 5271-7.

Huang, C., et al., Inhibition of benzo(a)pyrene diol-epoxide-induced transactivation of activated protein 1 and nuclear factor kappaB by black raspberry extracts. Cancer Res, 2002. 62(23): p. 6857-63.

Katsube, N., et al., Induction of apoptosis in cancer cells by Bilberry (*Vaccinium myrtillus*) and the anthocyanins. J Agric Food Chem, 2003. 51(1): p. 68-75.

Liu, M., et al., Antioxidant and antiproliferative activities of raspberries. J Agric Food Chem, 2002. 50(10): p. 2926-30.

Malik, M., et al., Anthocyanin-rich extract from *Aronia meloncarpa* E induces a cell cycle block in colon cancer but not normal colonic cells. Nutr Cancer, 2003. 46(2): p. 186-96.

Felgines, C., et al., Blackberry anthocyanins are mainly recovered from urine as methylated and glucuronidated conjugates in humans. J Agric Food Chem, 2005. 53(20): p. 7721-7.

Nielsen, I.L., et al., Quantification of anthocyanins in commercial black currant juices by simple high-performance liquid chromatography. Investigation of their pH stability and antioxidative potency. J Agric Food Chem, 2003. 51(20): p. 5861-6.

Olsson, M.E., et al., Inhibition of cancer cell proliferation in vitro by fruit and berry extracts and correlations with antioxidant levels. J Agric Food Chem, 2004. 52(24): p. 7264-71.

Olsson, M.E, et al., Antioxidant levels and inhibition of cancer cell proliferation in vitro by extracts from organically and conventionally cultivated strawberries. J Agric Food Chem, 2006. 54(4): p. 1248-55.

Parry, J., et al., Chemical compositions, antioxidant capacities, and antiproliferative activities of selected fruit seed flours. J Agric Food Chem, 2006. 54(11): p. 3773-8.

Pergola, C., at al., Inhibition of nitric oxide biosynthesis by anthocyanin fraction of blackberry extract. Nitric Oxide, 2006. 15(1): p. 30-9.

Proteggente, A.R., et al., The antioxidant activity of regularly consumed fruit and vegetables reflects their phenolic and vitamin C composition. Free Radio Res, 2002. 36(2): p. 217-33.

Re, R., et al., Antioxidant activity applying an improved ABTS radical cation decolorization assay. Free Radic Biol Med, 1999. 26(9-10): p. 1231-7.

Reddy, M.K., R.L. Alexander-Lindo, and M.G. Nair, Relative inhibition of lipid peroxidation, cyclooxygenase enzymes, and human tumor cell proliferation by natural food colors. J Agric Food Chem, 2005. 53(23): p. 9268-73.

Rice-Evans, C.A., et al., The relative antioxidant activities of plant-derived polyphenolic flavonoids. Free Radic Res, 1995. 22(4): p. 375-83.

Rodrigo, K.A., et al., Suppression of the tumorigenic phenotype in human oral squamous cell carcinoma cells by an ethanol extract derived from freeze-dried black raspberries. Nutr Cancer, 2006. 54(1): p. 58-68.

Rossi, A., et al., Protective effects of anthocyanins from blackberry in a rat model of acute lung inflammation, Free Radic Res, 2003. 37(8): p. 891-900.

Rubinskiene, M., et al., HPLC determination of the composition and stability of blackcurrant anthocyanins. J Chromatogr Sci, 2005. 43(9): p. 478-82.

Sellappan, S., C.C. Akoh, and G. Krewer, Phenolic compounds and antioxidant capacity of Georgia-grown blueberries and blackberries. J Agric Food Chem, 2002. 50(8): p. 2432-8.

Seeram, N.P., et al., Total cranberry extract versus its phytochemical constituents: antiproliferative and synergistic effects against human tumor cell lines. J Agric Food Chem, 2004. 52(9): p. 2512-7.

Seeram, N.P., et al., Cyclooxygenase inhibitory and antioxidant cyanidin glycosides in cherries and berries. Phytomedicine, 2001. 8(5): p. 362-9.

Stintzing, F.C., et al., A novel zwitterionic anthocyanin from evergreen blackberry (*Rubus laciniatus* Willd.). J Agric Food Chem, 2002. 50(2): p. 396-9.

Tsao, R. and R. Yang, Optimization of a new mobile phase to know the complex and real PolYPhenolic composition: towards a total phenolic index using high-performance liquid chromatography. J Chromatogr A, 2003. 1018(1): p. 29-40.

Visconti, A., et al., Cytotoxic and immunotoxic effects of *Fusarium* mycotoxins using a rapid calorimetric bioassay. Mycopathologia, 1991. 113(3): p. 181-6.

Wang, H., G. Cao, and R.L. Prior, Oxygen Absorbing Capacity of Anthocyanins. J Agric Food Chem, 1997. 45(2): p. 304-309.

Wang, H., et al., Antioxidant and antiinflammatory activities of anthocyanins and their aglycon, cyanidin, from tart cherries. J Nat Prod, 1999. 62(5).

Wang, S.Y., et al., Antioxidant activity in lingonberries (*Vaccinium vities-idaea* L.) and its inhibitory effect on activator protein-1, nuclear factor-kappaB, and mitogen-activated protein kinases activation. J Agric Food Chem, 2005. 53(8): p. 3156-66.

Wang, J. and G. Mazza, Effects of anthocyanins and other phenolic compounds on the production of tumor necrosis factor alpha in LPS/IFN-gamma-activated RAW 264.7 macrophages. J Agric Food Chem, 2002. 50(15): p. 4183-9.

Wang, J. and G. Mazza, Inhibitory effects of anthocyanins and other phenolic compounds on nitric oxide production in LPS/IFN-gamma-activated RAW 264.7 macrophages. J Agric Food Chem, 2002. 50(4): p. 850-7.

Xue, H., et al., Inhibition of cellular transformation by berry extracts. Carcinogenesis, 2001. 22(2): p. 351-6.

Yi, W., J. Fischer, and C.C. Akoh, Study of anticancer activities of muscadine grape phenolics in vitro. J Agric Food Chem, 2005. 53(22): 8804-12.

Youdim, K.A., et al., Potential role of dietary flavonoids in reducing microvascular endothelium vulnerability to oxidative and inflammatory insults ( small star, filled). J Nutr Biochem, 2002. 13(5): p. 282-288.

Zhang, Y., S.K. Vareed, and M.G. Nair, Human tumor cell growth inhibition by nontoxic anthocyanidins, the pigments in fruits and vegetables. Life Sci, 2005. 76(13): p. 1465-72.

Zhao, C., et at., Effects of commercial anthocyanin-rich extracts on colonic cancer and nontumorigenic colonic cell growth. J Agric Food Chem, 2004. 52(20): p. 6122-8.

Amorini, A.M., et al., Activity and mechanism of the antioxidant properties of cyanidin-3-O-beta-glucopyranoside. Free Radio Res, 2001. 35(6): p. 953-66.

Jing, P. and M.M. Giusti, Effects of extraction conditions on improving the yield and quality of an anthocyanin-rich purple corn (*Zea mays* L.) color extract. J Food Sci, 2007. 72(7): p. C363-81.

Seeram, N.P., et al., Blackberry, black raspberry, blueberry, cranberry, red raspberry, and strawberry extracts inhibit growth and stimulate apoptosis of human cancer cells in vitro. J Agric Food Chem, 2006, 54(25): p. 9329-39.

Macheix, JJ et al., Frit Phenolics. CRC Press: Boca Raton, FL. 1990.

Serraino, I., et al., Protective effects of cyanidin-3-O-glucoside from blackberry extract against peroxynitrite-induced endothelial dysfunction and vascular failure. Life Sci, 2003. 73(9): p. 1097-114.

Siriwoharn, T., et al., Influence of cultivar, maturity, and sampling on blackberry (*Rubus l.* Hybrids) anthocyanins, polyphenolics, and antioxidant properties. J Agric Food Chem, 2004. 52(26): p. 8021-30.

Stintzing, F.C., et al., Color and antioxidant properties of cyanidin-based anthocyanin pigments. J Agric Food Chem, 2002. 50(21): p. 6172-81.

Sautebin, L., et al., Effect of anthocyanins contained in a blackberry extract on the circulatory failure and multiple organ dysfunction caused by endotoxin in the rat. Planta Med, 2004. 70(8): p. 745-52.

Wada, L. and B. Ou, Antioxidant activity and phenolic content of Oregon caneberries. J Agric Food Chem, 2002. 50(12): p. 3495-500.

Thole, J.M., et al., A comparative evaluation of the anticancer properties of European and American elderberry fruits. J Med Food, 2006. 9(4): p. 498-504.

Wang, S.Y. and H.S. Lin, Antioxidant activity in fruits and leaves of blackberry, and strawberry varies with cultivar and developmental stage. J Agric Food, 2000. 48(2): p. 140-6.

Feng, R., et al., Blackberry extracts inhibit activating protein 1 activation and cell transformation by perturbing the mitogenic signaling pathway. Nutr Cancer, 2004. 50(1): p. 80-9.

Rossi, A., et al., Protective effects of anthocyanins from blackberry in a rat model of acute lung inflammation. Free Radic Res, 2003. 37(8): p. 891-900.

Bagchi, D., et al., Anti-angiogenic, antioxidant, and anti-carcinogenic properties of a novel anthocyanin-rich berry extract formula. Biochemistry (Mosc), 2004. 69(1): p. 75-80, 1 p. preceding 75.

Cacace, J.E. and G. Mazza, Extraction of anthocyanins and other phenolics from black currants with sulfured water. J Agric Food Chem, 2002. 50(21): p. 5939-46.

Chen, F., et al., Optimization of ultrasound-assisted extraction of anthocyanins in red raspberries and identification of anthocyanins in extract using high-performance liquid chromatography-mass spectrometry. Ultrason Sonochem, 2007. 14(6): p. 767-78.

Cho, M., et al., Flavonoid glycosides and antioxidant capacity of various blackberry, blueberry and red grape genotypes determined by high-performance liquid chromatography/mass spectrometry. Journal of the Science of Food and Agriculture, 2004. 84: p. 1771-1782.

Chun, O.K., et al., Contribution of individual polyphenolics to total antioxidant capacity of plums. J Agric Food Chem, 2003. 51(25): p. 7240-5.

Coyner, M.A. et al., Thornlessness in Blackberries: A Review. Small Fruits Review, vol. 4(2), 2005. p. 83-106.

Ding, M., et al., Cyanidin-3-glucoside, a natural product derived from blackberry, exhibits chemopreventive and chemotherapeutic activity. J Biol Chem, 2006. 281(25): p. 17359-68.

Felgines, C., et al., Blackberry anthocyanins are slightly bioavailable in rats. J Nutr, 2002. 132(6): p. 1249-53.

Raynal, J. et al., Intervention of Phenolic Compounds in Plum Technology. 2. Mechanisms of anthocyanin Degradation. J. Agric. Food Chem, 1989, 37, 1051-1053.

Fukumoto, L.R. and G. Mazza, Assessing antioxidant and prooxidant activities of phenolic compounds. J Agric Food Chem, 2000. 48(8): p. 3597-604.

Garcia-Alonso, M., et al., Evaluation of the antioxidant properties of fruits. Food Chemistry, 2004. 84: p. 13-18.

Hager, T.J., et al., Ellagitannin composition of blackberry as determined by HPLC-ESI-MS and MALDI-TOF-MS. J Agric Food Chem, 2008. 56(3): p. 661-9.

Ju, Z.Y. and L.R. Howard, Effects of solvent and temperature on pressurized liquid extraction of anthocyanins and total phenolics from dried red grape skin. J Agric Food Chem, 2003. 51(18): p. 5207-13.

Kang, S.Y., et al., Tart cherry anthocyanins inhibit tumor development in Apc(Min) mice and reduce proliferation of human colon cancer cells. Cancer Lett, 2003. 194(1): p. 13-9.

Kapasakalidis, P.G., R.A. Rastail, and M.H. Gordon, Extraction of polyphenols from processed black currant (*Ribes nigrum* L.) residues. J Agric Food Chem, 2006. 54(11): p. 4016-21.

Seeram, N.P., et al., Characterization, quantification, and bioactivities of anthocyanins in *Cornus* species. J Agric Food Chem, 2002. 50(9): p. 2519-23.

Koide, T., et al., Antitumor effect of anthocyanin fractions extracted from red soybeans and red beans in vitro and in vivo. Cancer Biother Radiopharm, 1997. 12(4): p. 277-80.

Liu, R.N., Potential synergy of phytochemicals in cancer prevention: mechanism of action. J Nutr, 2004. 134(12 Suppl): p. 3479S-3485S.

McDougall, G.J., et al., Anthocyanins from red wine—their stability under simulated gastrointestinal digestion. Phytochemistry, 2005. 66(21): p. 2540-8.

Mertz, C., et al., Analysis of phenolic compounds in two blackberry species (*Rubus glaucus* and *Rubus adenotrichus*) by high-performance liquid chromatography with diode array detection and electrospray ion trap mass spectrometry. J Agric Food Chem, 2007. 55(21): p. 8616-24.

Moyer, R.A., et al., Anthocyanins, phenolics, and antioxidant capacity in diverse small fruits: vaccinium, rubus, and ribes. J Agric Food Chem, 2002. 50(3): p. 519-25.

Ohgami, K., et al., Anti-inflammatory effects of aronia extract on rat endotoxin-induced uveitis. Invest Ophthalmol Vis Sci, 2005. 46(1): p. 275-81.

Pantelidis, G.E., Vasilakakis, M., Manganaris G. A., Diamantidis Gr., Antioxidant capacity, phenol, anthocyanin and ascorbic acid contents in raspberries, blackberries, gooseberries and Cornelian cherries. Food Chemistry, 2007. 102: p. 777-783.

Pinelo, M., et al., Effect of clarification techniques and rat intestinal extract incubation on phenolic composition and antioxidant activity of black currant juice. J Agric Food Chem, 2006. 54(18): p. 6564-71.

Naczk M et al "Extraction and analysis of phenolics in food" Journal of Chromatography, Elsevier Science Publishers B.V, NL vol. 1054, No. 1-2, Oct. 29, 2004, pp. 95-111 XP004607004 ISSN: 0021-9673.

Dao Lan T et al "Improved method for the stabilization of anthocyanidins" Journal of Agricultural and Food Chemistry vol. 46, No. 9, Sep. 1998, pp. 3564-356 XP002572883 ISSN: 0021-8561.

Jiao Zhonggao et al "Antioxidant activities of total pigment extract from blackberries" Food Technology and Biotechnology vol. 43, No. 1, Jan. 2005, pp. 97-102 XP002572884 ISSN: 1330-9862.

D.C. Estuupinan, S.J. Schwartz and G.A. Garzon "Antioxidant Activity, Total Phenolics Content, Anthocyanin and Color Stability of Isotonic Model Beverages Colored . . . " Journal of Food and Science, vol. 76, 2011.

* cited by examiner

A)

B)

A)

B)

BERRY PREPARATIONS AND EXTRACTS

This application is a continuation-in-part utility patent application which claims priority to U.S. patent application Ser. No. 12/088,156 filed on Mar. 26, 2008 (issued as U.S. Pat. No. 7,964,223), which in turn is a national stage application of international patent appl. no. PCT/US06/37237 filed on Sep. 26, 2006 and claiming the benefit of priority in U.S. Provisional Patent Appl. Ser. No. 60/720,892 filed on Sep. 27, 2005, the disclosures of each of which are incorporated in their entirety herein by reference.

TECHNICAL FIELD

The present invention relates to compositions having antioxidant and anti-inflammatory activity, derived from a berry. In particular, the invention relates to a method for deriving an extract having antioxidant and anti-inflammatory activity from a berry, and to formulated compositions derived by the method for oral and topical administration. Still further, the invention provides methods and compositions for treatment of inflammation, oxidative stress, or cancer comprising administering an effective amount of the composition of the invention.

BACKGROUND OF THE INVENTION

Polyphenolics (also known as phenolics) are metabolites found in plants, fruits, and vegetables. Phenolics have a number of functions including acting as free radical scavengers. Thus, phenolics disrupt many biological processes. The most notable type of phenolics are flavonoids which consist of proanthocyanidins, anthocyanidins, flavones, flavonols and their glycosides (Macheix, 1990). Anthocyanins are responsible for the red, purple, and blue colors of many fruits and vegetables. The term anthocyanin refers to a group of pigments found in plants, fruits, and vegetables that can be classified as both flavonoid and phenolic. Anthocyanins are not found in animals, microorganisms, or marine plants. It is thought that anthocyanins function by attracting insects to promote pollination but also to protect the plants from damage caused by ultraviolet (UV) radiation. Anthocyanins are glycosides of polyhydroxyl and polymethoxyl derivatives of 2-phenylbenzopyrylium or flavylium salts, and are soluble in water. The anthocyanins are electron deficient, and are therefore are strong scavengers for reactive oxygen species (ROS) such as free radicals. Although there are hundreds of different anthocyanins found in nature, six anthocyanin compounds predominate including: delphinidin, petunidin, cyanidin, pelargonidin, peonidin, and malvidin. The daily intake of anthocyanins in the United States is about 180-215 mg/day, and constitute the largest intake of phenolic compounds (Hertog, 1993).

Anthocyanins originally drew interest due to their role in color degradation in fruits, and their potential use as natural food colorants. More recently, anthocyanins have received attention because of their possible health benefits as natural antioxidant and anti-inflammatory compounds, and potentially as anti-cancer compounds. Antioxidant property, effects, or activity refers to compositions that inhibit, reduce, or reverse oxidation or the effects of oxidation, such as for example the oxidative process caused by free radicals. A free radical may be any chemical species that includes one or more unpaired electrons, and without limitations includes chemicals such as hydroxyl radical, superoxide radical, nitric oxide, and nitrogen dioxide. Examples of conditions involving free radical oxidative damage include, but are not limited to, aging, disease, stress, ultraviolet radiation, exercise, cancer, smoking, atherosclerosis, and chronic inflammation. Studies showed that antioxidant activity of cyanidins was greater than that of vitamin E and Trolox, and comparable to that of butylated hydroxytoluene (BHT) and butylated hydroxyanisole (BHA) (Wang et al., 1997; Rice-Evans et al., 1995; Liu et al., 2002; Proteggente et al., 2002; Wang et al., 1999).

Inflammation, or the biological state of being inflamed, is generally characterized by pain, redness, and swelling, and may result from physical causes such as injury, chemical causes such as exogenous substances including toxins, or biological causes such as infection by a virus, a bacteria, a parasite, or other disease-causing agent. As examples, various conditions associated with inflammation of the gastrointestinal tract are known, including but not limited to acute or chronic conditions or diseases such as inflammatory bowel disease, gastroesophageal reflux disease, diarrhea, radiation-induced enteritis, chemotherapy-induced enteritis, Crohn's disease, irritable bowel syndrome, diverticulitis, ulcers, colitis, viral infection, bacterial infection, and parasitic infection or infestation. In individuals afflicted with the above and similar conditions, affected cells such as dendritic cells, monocytes, macrophages, fibroblasts, endothelial cells, and T cells release causative agents, including cytokines such as interleukins (IL), tumor necrosis factor (TNF), interferons (IFN), and the like which trigger inflammation and/or an inflammatory response. Cytokines important in inflammation include, but are not limited to, IL-1, IL-6, IL-12, TNF-$\alpha$, and IFN-$\alpha$. Anti-inflammatory properties, effects, or activity refers to reducing inflammation and promoting healing of cells and tissues subject to inflammation and/or inflammatory processes.

Anti-cancer property, effect, or activity refers to a property of a substance, chemical, or material that can slow the proliferation of tumor cells (termed anti-proliferative effect), or kill tumor cells (termed cytotoxic effect). Recent studies have shown also that berries such as black raspberries possess cancer-preventing properties at both in-vitro and in-vivo levels (Kresty et al., 2001; Castro et al., 2002; Xue et al., 2001; Huang et al., 2002; Rodrigo et al, in press; U.S. patent application Ser. No. 10/951,413). In particular, anthocyanins have been shown to demonstrate a wealth of chemopreventive properties (Hecht et al., in press; Liu et al., 2002; Katsube et al., 2003; Hu et al., 2003).

However, anthocyanin compounds are inherently unstable both in vivo and in vitro, and tend to degrade over time, negating any health or medical benefits associated therewith (Rubinskiene et al., 2005; Nielsen et al., 2003; Morais et al., 2002). A need in the art therefore exists for methods for preparing compositions from anthocyanin-containing fruits such as berries which provide a stable anthocyanin content. Still further, there is a need for compositions including such stable anthocyanin compositions to provide health and medical benefits to individuals utilizing them. In particular, compositions formulated for oral administration and topical administration are described herein. However, it will be appreciated that other formulations are contemplated and can be derived by the skilled artisan from the teachings herein using methods known in the art, including injectable formulations. Accordingly, the present invention contemplates also injectable formulations including, but not limited to, solutions, suspensions, emulsion, microemulsions, micelles, liposomes, nanoparticles, microparticles, implants, depots, and polymer conjugates.

SUMMARY OF THE INVENTION

The present invention provides methods for deriving stable compositions from blackberries, and compositions incorporating such stable compositions. In one aspect, a method is provided for preparing a composition having antioxidant and anti-inflammatory activity, comprising exposing a berry to a solvent composition having a pH of from about 1 to about 3, adding a cryoprotectant, and recovering a berry extract having a stable anthocyanin content. The berry may be a blackberry. In one embodiment, the method comprises the steps of physically disrupting a quantity of berries, exposing the physically disrupted berries to the solvent composition, recovering a berry extract having a pH of from about 1.0 to about 4.5, and adding a cryoprotectant. The cryoprotectant is added in an amount of at least 2:1 (w/w) cryoprotectant:berry extract. The berry extract so provided typically comprises at least one stable anthocyanin in an amount effective to provide antioxidant and anti-inflammatory activity. In another embodiment, the recovered berry extract has a pH of about 3.5. The physically disrupted berries may be dewatered prior to being exposed to the solvent composition, after being exposed to the solvent composition, or both.

In another aspect, the present invention provides stabilized compositions having antioxidant and anti-inflammatory activity, prepared by the method of the invention as described above. In one embodiment, a composition is provided having antioxidant and anti-inflammatory activity, comprising a berry extract having at least one stable anthocyanin in an amount effective to provide antioxidant and anti-inflammatory activity. The berry extract is provided by the steps of physically disrupting a quantity of berries and exposing the physically disrupted berries to a solvent composition having a pH of from about 1 to about 3, and adding a cryoprotectant, which stabilizes the at least one anthocyanin. The cryoprotectant is added in an amount of at least 2:1 (w/w) cryoprotectant:berry extract. The berry extract may be derived from a blackberry. Compositions comprising the berry extract of the present invention, formulated for oral and/or topical administration, are provided also, including without limitation nutritional supplements, capsules, tablets, chewing gum, lotions, creams, mucoadhesive gels, vanishing lotions, vanishing creams, and the like.

In yet another aspect, the present invention provides methods for treatment of inflammation, oxidative stress, or cancer in a mammal in need thereof, comprising administering an effective amount of the composition of the invention. Still yet further, another aspect of the invention is compositions comprising a therapeutically effective amount of the composition of the invention, formulated in a pharmaceutically acceptable vehicle. The composition may be provided in combination with additional anticancer agents, additional anti-oxidant agents, and/or additional anti-inflammatory agents.

As should be appreciated, the embodiments shown and described herein are an illustration of one of the modes best suited to carry out the invention. It will be realized that the invention is capable of other different embodiments and its several details are capable of modification in various, obvious aspects all without departing from the invention. Accordingly, the drawings and descriptions will be regarded as illustrative in nature, and not as restrictive. Unless otherwise indicated, all patents, patent applications, and non-patent documents referenced in the present disclosure are incorporated herein by reference in their entirety.

BRIEF DESCRIPTION OF THE DRAWINGS

The accompanying drawings incorporated in and forming a part of the specification, illustrate several aspects of the present invention and together with the description serve to explain the principles of the invention. In the drawings.

Figure 1:
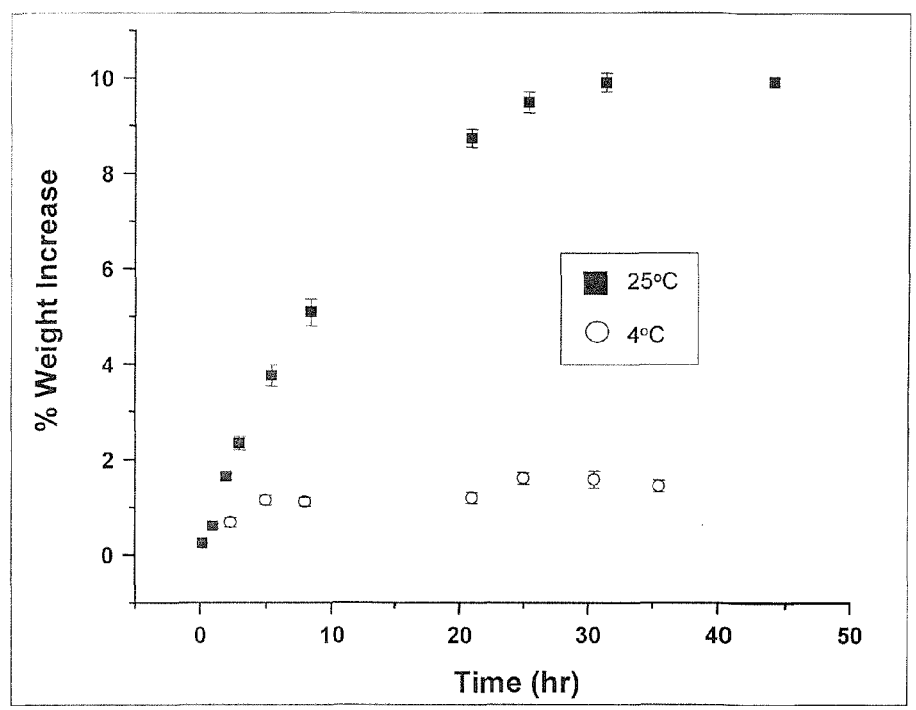
FIG. 1 shows percent weight increase of active blackberry powder as a function of time when stored at 25° C. and at 4° C.

Reference will now be made in detail to the present preferred embodiment of the invention, an example of which is illustrated in the accompanying drawings.

DETAILED DESCRIPTION OF THE INVENTION

Blackberries and raspberries, sometimes referred to as "brambles", are a species of fruit in the genus *Rubus*. *Rubus* is quite diverse and has 12 subgenera with several of the subgenera having more than a hundred species. In the United States, *R. allegheniensis, R. argutus, R. cuneifolius, R. Canadensis*, and *R. trivialis* are the dominant *Rubus* species. Blackberries belong to the subgenus *Eubatus*, and have much greater complexity than raspberries in terms of genetic background, growth characteristics, and number of species. Blackberries are native to Asia, Europe, North and South America. They have been grown in Europe for over 2000 years as food and for medical applications. Blackberries grow in three different forms: trailing, semi-erect, and erect. In the eastern half of the United States, the dominate form is the erect including the thorny types, Cherokee, Comanche, Cheyenne, Darrow, Illini Hardy Blackberry, Shawnee, and Choctaw. The thornless cultivars include Hull, Chester, Navaho, and Arapaho. Other types of blackberries include, but are not limited to, Eldorado, Ebony King, Raven, Ranger, Hedrick, Bailey, and Brazos. Semi-erect blackberries requiring a trellis for production include Black Satin, Chester, Dirksen, Hull Thornless, Smoothstem, and Thornfree. In the Pacific Northwest, blackberries are often called Marionberries. Other berries that have genetic similarity to blackberries include Boysenberry, Loganberry, Olallieberry, and Youngberry. A 2002 report by the USDA lists the total US production of all blackberry types to be about 56 million pounds grown on 8370 acres. According to the USDA, of the blackberries harvested in the US, about 40% are used for jams and jellies, 25% for bakery products, 23% frozen or canned, and the 12% for juices or other food.

Tsao et al. (2003) showed that, relative to other fruits, blackberries have high concentrations of polyphenolics such as anthocyanins with as much as 1923 µg/g wet fruit. Sellappan et al. (2002) showed that blackberries had high concentrations of ellagic acid; Chocktaw had 33.81 mg/100 g berry and Kiowa had 30.01 mg/100 g berry. Blackberries were also found to contain flavonoids, with the major flavonoid, catechin, present in Choctaw at 312.86 mg/100 g berry. Sellappan showed that the average total anthocyanin and polyphenolic content in blackberries was 116.59±8.58 mg/100 g berry and 486.53±97.13 mg/100 g berry, respectively.

Accordingly, in one embodiment the present invention describes methods for deriving stable compositions from blackberries, and compositions made by those methods. However, it will easily be understood by those skilled in the art that the methods and compositions taught in this invention apply to many other types of fruits, plants, and vegetables having an anthocyanin content, including but not limited to: strawberries, black raspberries, apple, crabapple, chokeberry, Hawthorn, Juneberry, Loquat, pear, apricot, cherry, plum, peach, various other raspberries, cloudbeny, wineberry, salmonberry, bearberry, bilberry, cranberry, huckleberry, barberry, currant, elderberry, gooseberry, hackberry, honeysuckle, nannyberry, sheepberry, sea grape, wolfberry, crowbeny, goumi, kiwi, various other grapes, thimbleberry, salmonberry, various types of melons such as watermelon, fig, lime, avocado, feijoa, guava, kumquat, longan, lychee, passion fruit, and pineapple.

In one aspect, the present invention provides a method for preparing a composition having antioxidant and anti-inflammatory activity, comprising exposing a berry to a solvent composition having a pH of from about 1 to about 3, adding a cryoprotectant, and recovering a berry extract having a stabilized anthocyanin content. As discussed above, the berry may be a blackberry. In one embodiment, the method comprises the steps of: physically disrupting a quantity of berries, exposing the physically disrupted berries to the solvent composition, recovering a berry extract having a pH of from about 1.0 to about 4.5, and adding a cryoprotectant. Suitable cryoprotectants include, but are not limited to, monosaccharides such as glucose, fructose, maltose, ribose, mannose, and xylose, disaccharides such as trehalose, sucrose, myoinositol, phosphorylated inositols, and glycerol, polysaccharides such as hydroxyethyl starch and other starches, dextran, and hyaluronic acid, and polymers such as polyvinylpyrrolidone, alginates, carrageenan, cyclodextrins, polyvinyl alcohol, cellulose-derivatives such as carboxymethyl cellulose, methyl cellulose, hydroxypropyl cellulose, hydroxypropylmethyl cellulose, xanthan gum, and chitosan. It will be appreciated that the final pH of the extract will depend on both the concentration of the berry extract in the solvent composition and on the specific solvent composition used for extraction. The berry extract so recovered typically comprises at least one stabilized anthocyanin in an amount effective to provide antioxidant and anti-inflammatory activity. In another embodiment, the recovered berry extract has a pH of about 3.5. The stabilized anthocyanin may be a delphinidin, a petunidin, a cyanidin, a pelargonidin, a peonidin, a malvidin, or any combination thereof.

The physically disrupted berries may be exposed to a solvent composition comprising an alcohol and at least one acid, with the acid provided in a sufficient amount whereby the solvent composition has a pH of from about 1 to about 3. The acid may be provided in an amount of from about 0.005% to about 3% (v/v) of the alcohol. In one embodiment, the acid is provided in an amount of from about 0.01% to about 2% of the alcohol (v/v). In yet another embodiment, the acid is provided from about 0.01% to about 1% of the alcohol (v/v). Any of a number of alcohols may be suitable for the present invention, including, but not limited to, lower chain alcohols such as methanol, ethanol, propanol, butanol, and mixtures thereof. The acid may be any acid suitable for providing the desired pH for the solvent composition, including, but not limited to, hydrochloric acid, acetic acid, citric acid, lactic acid, trifluoroacetic acid, aspartic acid, glutamic acid, sulfur-containing acids such as sulfonic acid, phosphoric acid, maleic acid, and mixtures thereof. In yet another embodiment, the alcohol can be replaced with a suitable ketone or a suitable halogenated olefin, such as acetone, chloroform, methylene chloride, or mixtures thereof.

The physically disrupted berries may be dewatered to a residual water content of up to 20% (w/v) prior to being exposed to the solvent composition, after being exposed to the solvent composition, or both. In one embodiment, the physically disrupted berries are dewatered to a residual water content of up to 10% (w/v). It will be appreciated that any suitable method may be employed for dewatering, such as heating or centrifuging a berry puree to remove water, followed by crushing the dried berry puree to a powder. Typically, a powder in accordance with the present invention is prepared by lyophilization or freeze-drying, i.e., freezing followed by removal of water by sublimation. Beneficially, freeze-drying provides a chemically and physically stable, free-flowing dry powder.

In another aspect, the present invention provides compositions having antioxidant and anti-inflammatory activity, prepared by the method of the invention as described above. In one embodiment, a composition is provided having antioxidant and anti-inflammatory activity, comprising a berry extract having at least one stabilized anthocyanin in an amount effective to provide antioxidant and anti-inflammatory activity. The berry extract may be provided by the steps of physically disrupting a quantity of berries, exposing the physically disrupted berries to a solvent composition, and adding a cryoprotectant, which stabilizes the at least one anthocyanin. Suitable cryoprotectants include, but are not limited to, monosaccharides such as glucose, fructose, maltose, ribose, mannose, and xylose, disaccharides such as trehalose, sucrose, myoinositol, phosphorylated inositols, and glycerol, polysaccharides such as hydroxyethyl starch and other starches, dextran, and hyaluronic acid, and polymers such as polyvinylpyrrolidone, alginates, carrageenan, cyclodextrins, polyvinyl alcohol, cellulose-derivatives such as carboxymethyl cellulose, methyl cellulose, hydroxypropyl cellulose, hydroxypropylmethyl cellulose, xanthan gum, and chitosan. The berry extract may be derived from a blackberry. In one embodiment, the berry extract has a pH of from about 1.0 to about 4.5. In another embodiment, the berry extract has a pH of about 3.5. The stabilized anthocyanin may be a delphinidin, a petunidin, a cyanidin, a pelargonidin, a peonidin, a malvidin, and combinations thereof.

The solvent composition may comprise an alcohol and at least one acid, wherein the acid is provided in an amount sufficient wherein a pH of the solvent composition is from about 1 to about 3. The acid may be provided in an amount of from about 0.005% to about 3% (v/v) of the alcohol. The alcohol may be any suitable alcohol, including but not limited to lower chain alcohols such as methanol, ethanol, propanol, butanol, and mixtures thereof. The acid may be any acid suitable for providing the desired pH of the solvent composition, including, but not limited to, hydrochloric acid, acetic acid, citric acid, lactic acid, trifluoroacetic acid, aspartic acid, glutamic acid, formic acid, phosphoric acid, maleic acid, and combinations thereof. Optionally, in place of the alcohol a suitable ketone or a suitable halogenated olefin may be used, such as acetone, chloroform, methylene chloride, and mixtures thereof. As discussed above, the physically disrupted berries may be dewatered to a water content of up to 20%

(w/v), such as by freeze-drying, either prior to exposing to the solvent composition, after exposing to the solvent composition, or both.

A variety of formulations for oral and/or topical administration are contemplated for the composition of the present invention. In one embodiment, a formulation for oral administration is provided, comprising the berry extract in an amount of from about 3% (w/w) to about 90% (w/w). In another embodiment, a formulation for topical administration is provided, comprising the berry extract in an amount of from about 1% (w/w) to about 20% (w/w). It will be appreciated by the skilled artisan that a large number of topical and oral formulations are known in the art, such as nutritional supplements, capsules, enteric-coated capsules, film-coated capsules, tablets, enteric-coated tablets, film-coated tablets, chewing gums, lotions, creams, mucoadhesive gels, vanishing lotions, vanishing creams, and the like. Other ways to apply a composition topically formulations are known, including but not limited to: sprays, ointments, gels, patches, and needle-free devices that deliver their contents by diffusion, mechanical or gas-driven energy. The making of such formulations and/or devices is well within the ability of the skilled artisan, and such formulations and methods are contemplated also by the present invention.

For example, it is known to provide compositions in emulsion or microemulsion form, as lotions and/or creams. A lotion refers to a semi-viscous emulsion that is meant to be applied to the skin. A cream refers to a more viscous emulsion that is also meant to be applied to the skin. Lotions and creams may be of the oil-in-water or water-in-oil type. In one embodiment of the present invention, lotions and creams of the oil-in-water type are provided which stabilize a composition according to the present invention, and/or promote its penetration into or through the skin layers.

An emulsion refers to a biphasic opaque mixture of two immiscible liquids stabilized by a surfactant. Emulsions are thermodynamically unstable systems, and usually require the application of high-torque mechanical mixing or homogenization to produce dispersed droplets in the range of about 0.2 to 25 μm. In contrast, a microemulsion is a stable biphasic mixture of two immiscible liquids stabilized by a surfactant and usually a co-surfactant. Microemulsions are thermodynamically stable, isotropically clear, form spontaneously without excessive mixing, and have dispersed droplets in the range of about 5 nm to 140 nm. Both microemulsions and emulsions can be made as water-in-oil or oil-in-water systems. In a water-in-oil system, the dispersed phase is water and the continuous phase is oil. In an oil-in-water system, the dispersed phase is oil and the continuous phase is water. Whether water-in-oil or oil-in-water systems will form is largely influenced by the properties of the surfactant. The use of surfactants that have hydrophilic-lipophilic balances (HLB) of about 3-6 tend to promote the formation of water-in-oil microemulsions while those with HLB values of about 8-18 tend to promote the formation of oil-in-water microemulsions.

Formulations contemplated for oral administration directly to the gastrointestinal tract include, but are not limited to, nutritional supplements, capsules, enteric-coated capsules, film-coated capsules, tablets, enteric-coated tablets, film-coated tablets, chewing gums, caplets, solutions, and suspensions. It is envisioned that more novel particle-based suspensions for oral administration can be produced, such as emulsions, microemulsions, nanoparticle or microparticle suspensions. It is also contemplated in this invention that a formulation for oral administration may be prepared that is delivered to and retained in the mouth, whereby the contents and/or the active ingredient primarily drain into the stomach. Formulations meeting these criteria include, but are not limited to, chewing gums, gels, sprays, lozenges, lollipops or other candies, rapidly dissolving strips, and the like. In one embodiment, the formulation for oral administration is a tablet or hard-gelatin capsule. In another embodiment, the formulation is coated with a substance to control the rate or location of disintegration, i.e., an enteric-coated or film-coated formulation.

The present invention contemplates providing enteric-coated oral formulations. An enteric-coating refers to a coating on an oral dosage form that is meant to cause the oral dosage form to remain intact in the lower pH of the stomach, but disintegrate once the dosage form reaches the higher pH of the intestines including the small intestines, large intestines, colon, or rectum. The most common enteric coatings are those that remain intact (undissociated) in the low pH of the stomach, but ionize when the pH is above pH 4-5, pH 5-7, or even above pH 7. Common enteric-coating materials include, but are not limited to, cellulose acetate phthalate, polyvinyl acetate phthalate, hydroxypropylmethyl cellulose phthalate, cellulose acetate trimellitate, carboxymethyl ethylcellulose, and hydroxypropyl methylcellulose acetate succinate, and polymethacrylates (methacrylic acid copolymer) including EUDRAGIT-based polymers. It is also contemplated to provide film-coated oral formulations. A film-coating typically targets the coated substance to the colon by remaining undissociated or stable until a pH 7 environment is reached. Film-coating materials to achieve this goal include, but are not limited to, EUDRAGIT-based polymers that are soluble in intestinal fluid at a pH greater than 7, pectin, amylose, and chitosan-based polymers.

It is also envisioned that a colon or tumor-specific film-coating can be used on the oral dosage form that effectively serves to increase the delivered concentration of the composition of the present invention by selective removal of the coating by an endogenous enzyme present in the target tissue of the small intestines, large intestines, colon, or rectum. Alternatively, it is envisioned that tumors in the colon or rectum can be targeted by coating the dosage form with a ligand specific for the tumor cell surface, i.e., without limitation an antibody or binding fragment thereof.

A chewing gum is a flavored composition that is meant to deliver a flavor or other substance by chewing. The primary part of chewing gum is the gum base, which is a non-nutritive substance. The gum base may consist of any one or more of the following; an elastic ingredient, a resin that acts as a binder and softener, a plasticizer, fillers, a sweetener or flavoring agent, and an antioxidant. As an example, Subpart G titled "Gum, Chewing Gum Bases and Related Substances" from The Code of Federal Regulations (Title 21, Volume 3, Subchapter B) lists ingredients that may be used in gums, including arabinogalactan, natural gum bases including chicle, chiquibul, crown gum, gutta hang kang, massaranduba balata, massaranduba chocolate, nispero, rosidinha, Venezuelan chicle, jelutong, leche capsi (sorva) perillo, leche de vaca, niger gutta, tunu, chilte, natural rubber (smoked sheet and latex solids), synthetic substances such as butadiene-styrene rubber, isobutylene-isoprene copolymer, paraffin, petroleum wax, petroleum wax synthetic, polyethylene, polyisobutylene, and polyvinyl acetate, plasticizing materials including glycerol ester of partially dimerized rosin, glycerol ester of partially hydrogenated gum or wood rosin, glycerol ester of polymerized rosin, glycerol ester of gum rosin, glycerol ester of tall oil rosin, glycerol ester of wood rosin, lanolin, methyl ester of rosin partially hydrogenated, pentaerythritol ester of partially hydrogenated gum or wood rosin, rice bran wax, stearic acid, sodium and potassium stearates, synthetic and natural terpene resins, antioxidants including butylated hydroxyanisole, butylated hydroxytoluene, propyl gallate, carrageenan, carrageenan with polysorbate 80, salts of carrageenan, furcelleran, salts of furcelleran, gellan gum, and xanthan gum. Of course, compositions in addition to those of the present invention may be included as is known in the art to provide desirable attributes for the gum, such as enjoyment (taste, mouth-feel, and the like), breath freshening, dental care, and oral care.

Still further, the compositions of the present invention may be provided along with a mucoadhesive polymer excipient, for direct delivery to a mucosal surface and also for transmucosal delivery into systemic circulation. Briefly, mucoadhesive polymer excipient refers to a polymer that has the ability to adhere to mucin. Typically, for the compositions of the present invention a mucoadhesive acidic polymer excipient is used, which when dissolved or suspended in water results in an acidic pH. In one embodiment, the mucoadhesive polymer will provide a polymer solution or suspension having a pH of from about 1 to about 4.5. The polymer may be non-ionic or anionic. Mucoadhesive polymer excipients will typically be selected which also control the rate of release of the active ingredient from the gel by providing a controlled rate of polymer rehydration. The mucoadhesive polymer excipient may be present in the dosage form in one embodiment in a weight percentage between 5-50%. In another embodiment, the excipient is present in a weight percentage between 5-20%. In yet another embodiment, the excipient is present in a weight percentage between 5-10%. As non-limiting examples, the mucoadhesive polymer excipient may be selected from one or more of the following polymers: polyacrylic acid, crosslinked polyacrylic acid, polyvinyl pyrrolidone, cross-linked polyvinyl pyrrolidone, polymethacrylic acid, polymethacrylic-acid co-polymers, carboxymethyl cellulose, cellulose or derivatives thereof, or alginate.

Of course, additional substances may be included in the formulations of the present invention to provide additional desired properties, such as sweeteners or preservatives. Sweeteners may be of natural original or synthetic, and may include, but are not limited to, fructose, glucose, glycerol, lactitol, maltitol, maltose, sorbitol, xylitol, saccharin, aspartame, cyclamate, sucralose, or acesuflame potassium, or mixtures thereof. Preservatives are natural or synthetic chemicals that are added to hinder spoilage, whether caused by microbial growth, or unwanted chemical changes such as, but not limited to, hydrolysis or oxidation. Suitable preservatives may include, but are not limited to, benzoic acid, sorbic acid, benzyl alcohol, benzethonium chloride, butyl paraben, cetrimide, chlorobutanol, cresol, ethyl paraben, phenol, phenoxyethanol, propylene glycol, sodium benzoate, thimersol, methyl paraben, propyl paraben, or mixtures thereof.

Still yet further, the present invention provides a method of treating inflammation, oxidative damage, or cancer, comprising administering to a mammal such as a human in need thereof an effective amount of a composition as described above. The inflammation may be associated with cancer, inflammatory bowel disease, gastroesophageal reflux disease, diarrhea, radiation-induced enteritis, chemotherapy-induced enteritis, Crohn's disease, irritable bowel syndrome, diverticulitis, ulcer, colitis, viral infection, bacterial infection, parasitic infection, and combinations thereof. The inflammation may be partially mediated by the release in the body of the mammal of at least one cytokine including, but not limited to, an interleukin such as IL-1, IL-6, or IL-12, or TNF-α, and IFN-α. The oxidative damage may be mediated at least partially by release of a free radical in the body of the mammal.

The cancer may be a skin cancer, an oral cancer, a cancer of the eye, a cancer of a mucosal surface such as the vagina, the nose, and the rectum, and combinations thereof. As described above, the composition may be formulated for administration by at least one of orally, topically, and by injection.

In yet still another aspect, the present invention provides compositions for treating inflammation, oxidative damage, or cancer in a mammal in need thereof, comprising a therapeutically effective amount of a composition as described above in a pharmaceutically acceptable vehicle. The composition may further comprise at least one additional anti-cancer agent, at least one additional anti-oxidant, at least one additional anti-inflammatory agent, and combinations thereof. The compositions may be formulated for administration by at least one of orally, topically, and by injection as described above.

The examples provided herein are presented in support of and to further illustrate the invention as described above and in the accompanying drawings, but are not to be considered as limited thereto. Citations of literature herein are incorporated into this disclosure by reference in their entirety unless otherwise indicated. Generally, 2,2-Azinobis(3-ethylbenzothiazoline-6-sulfonicacid)diammonium salt (ABTS), Trolox (6-hydroxy-2,5,7,8-tetramethychroman-2-carboxylic acid), potassium persulfate, formic acid (ACS, >96%), 3-(4,5-dimethyl-thiazol-2-yl)-2,5-diphenyl tetrazolium bromide (MTT), Folin and Ciocalteau phenol reagent and gallic acid (98% purity) were purchased from Sigma (St. Louis, Mo.). Hydrogen chloride ~1.25 M in ethanol was purchased from Fluka (St. Gallen, Switzerland). USP grade Ethanol (Absolute—200 proof) was purchased from AAPER Alcohol and Chemical Co. (Shelbyville, Ky.). HPLC grade acetonitrile was purchased from Fisher Scientific (Fair Lawn, N.J.).

EXAMPLE 1

A blackberry puree was prepared by pulping whole blackberries. For purposes of this disclosure, the term pulping refers to the process of removing the seeds and skin from whole fruit. However, it will be understood by those skilled in the art that the skin and seeds also contain many biologically useful substances and so it is envisioned that the skin and seeds may be retained for later use, or alternatively may be kept with the fruit pulp rather than separated.

Blackberries were picked from the vine and placed in containers for transporting to the picking station for inspection. The berries were not washed in order to prevent deterioration of the whole berry by surface water. The seeds and skin of the berries were removed using a Langsenkamp type 161 Colossal Pulper having two agitator arms with brushes with a stainless steel chamber, and stainless steel catch pan with two outlets (one threaded and one with a sanitary fitting) with a 10-horse power, 3 phase, 60 cycle, 230/460 volt meter. Whole blackberries were passed through the Lagsenkamp Pulper at a rate of 50-75 gallons/minute to produce a homogenous blackberry puree free of skin and seeds. The blackberry puree was stored frozen at −20° C.

EXAMPLE 2

A VirTis Model AD2 Lyophilizer was used to freeze-dry a blackberry puree, prepared as described in Example 1, to produce a free-flowing powder. The cycle used a freezer temperature of −40° C., a condenser temperature of −50° C., and vacuum of 200 mTorr. Approximately 10 g of blackberry puree in a glass lyophilization vial was freeze-dried. The following drying steps were used to prepare a purple cake of freeze-dried blackberry puree:

TABLE 1

Example Freeze-Drying Cycle for Blackberry Puree to Produce Active Pharmaceutical Powder

| Drying Steps | Temp (° C.) | Time (min) | Vacuum (mTorr) |
|---|---|---|---|
| 1 | −35 | 10 | 200 |
| 2 | −30 | 5 | 200 |
| 3 | −25 | 5 | 200 |
| 4 | −20 | 1200 | 200 |
| 5 | −15 | 840 | 200 |
| 6 | −10 | 10 | 200 |
| 7 | −5 | 10 | 200 |
| 8 | 0 | 10 | 200 |
| 9 | 5 | 120 | 200 |
| 10 | 10 | 300 | 200 |
| 11 | 15 | 10 | 200 |
| 12 | 20 | 180 | 200 |
| Post Heating | 25 | 90 | 200 |

The freeze-dried blackberry puree was collected from the glass lyophilization vial and milled using a mortar and pestle to produce a free-flowing reddish-purple powder.

EXAMPLE 3

A Hull lyophilizer was employed to create a second embodiment of a dry powder of the blackberry puree. A partially frozen blackberry puree (Example 1) (5204 g) was placed into the lyophilizer on metal pans in large chunks. The following lyophilization cycle shown in Table 2 was used to dry the blackberry puree:

TABLE 2

Lyophilization Cycle Used to Produce Freeze-Dried Blackberry Powder Steps

1. Freeze to −40° C.
2. Raise temp to −35° C.
3. Once at −35° C., hold for 3 hr
4. Set vacuum to less 150 microns
5. Raise temp to −10° C.
6. Once at −10° C., hold for 3 hr
7. Maintain vacuum of less than 150 microns
8. Raise temp to 0° C.
9. Once at 0° C., hold for 3 hr
10. Raise Temp to 5° C.
11. Once at 5° C., hold for 2.5 hr
12. Raise temp to 10° C.
13. Once at 10° C., hold for 2.4 hr
14. Raise temp to 20° C.
15. Once at 20° C., hold for 2.5 hr
16. Break vacuum The resulting blackberry powder weighed 559 g and was 10.7% w/w of the initial blackberry puree that was lyophilized. Next, 100 g of the freeze-dried blackberry powder was treated under sonication with 500 mL ethanol containing 0.01% HCl for 30 min to produce a blackberry extract having a pH in the range of 1.9-2.0. The suspension was filtered and the supernatant was collected in a flask. The supernatant was dried at 40° C. for 7 hr using a rotary evaporator. The recovered blackberry extract weighed 19.12 g or 19.12% w/w of the original 100 g dried blackberry powder.

EXAMPLE 4

Five hundred milligram portions of blackberry powder prepared as described in Example 2 were evaluated for rate of water sorption. Three vials were held at 25° C. and three vials were held at 4° C. The percentage weight increase over time due to water sorption was recorded for a period of 45 hr. As shown in FIG. 1, blackberry powder stored at 25° C. increased in weight by up to 10% by 30 hr, and then reached a plateau. In contrast, blackberry powder stored at 4° C. increased in weight by less than 1.7% and reached a plateau after only 5 hr.

EXAMPLE 5

Two different blackberry extracts were obtained by subjecting 2.5 g blackberry powder (Example 2) three times with either; sample A) 20 mL of ethanol/0.1% HCl or, sample B) 20 mL of ethanol/0.01% HCl under sonication. The three samples for each extraction condition were collected and centrifuged for 10 min at 12,000 g. The supernatant was then filtered to collect dark red solution. Ethanol was then removed at 40° C. using a rotary evaporator to obtain a dark red, viscous liquid. Ten (10) mL of water was added to sample A to produce a dark-red suspension having a pH of 1.2. Ten (10) mL of water was added to sample B to produce a dark-red suspension having a pH of 1.9. Both sample A and sample B were centrifuged for 10 min at 12,000 g and a final dark-red solution referred to berry extracts. As will be discussed in greater detail below, the resulting compositions are enriched for stabilized anthocyanins.

EXAMPLE 6

An aliquot of freeze-dried blackberry powder (2.5 g) prepared as described in Example 2 was treated under sonication for 30 min with 60 mL of ethanol containing 0.01% HCl. The supernatants were collected after filtration and dried by rotary evaporation at 40° C. The dried extract was dissolved in 10 mL of deionized water and filtered through a 1.0 μm nylon syringe filter. The blackberry extract had a pH of 1.9. The extract was either frozen at −20° C., or lyophilized to produce a dried blackberry extract (DBE) and then stored as a powder at −20° C. The average yield of DBE was 470.44±9.27 mg per gram of blackberry powder.

The blackberry extract was characterized for: i) monomeric anthocyanins and polymeric color measurement, ii) Total Phenolic Measurement, iii) Trolox Equivalent Antioxidant Capacity (TEAC) Assay, and iv) anthocyanin composition. Results of characterization for i, ii, and iii are shown in Table 3 below. It is important to note that the values for these several parameters are likely influenced by the extraction efficiency of the berry extract. Thus, it may be appreciated by those skilled in the art that a different extraction protocol may result in a berry extract that has different composition and features.

TABLE 3

Composition and Characterization of Dried Blackberry Extract (DBE)

| | Total Anthocyanins[a] (mg/g DBE) | Total Phenolics[b] (mg/g DBE) | Polymeric color (%) | TAC[c] (μM TE[d]/g DBE) |
|---|---|---|---|---|
| Blackberry extract (n = 3) | 6.80 ± 0.31 | 17.32 ± 0.74 | 2.2 ± 1.0 | 66.98 ± 1.27 |

[a]Total anthocyanins were expressed as cyanidin-3-glucoside equivalent.
[b]Total phenolics were expressed as gallic acid equivalent.
[c]TAC: total antioxidant capacity measured by Trolox-equivalent antioxidant capacity assay.
[d]TE: Trolox equivalent.

i) Monomeric Anthocyanins and Polymeric Color Measurement. Monomeric anthocyanin content was determined by the pH-differential method of Giusti and Wrolstad (2001). Briefly, samples were diluted 1:100 v/v in a 25 mM potassium chloride buffer (pH 1.0) and a 0.4 M sodium acetate buffer (pH 4.5), then read against a blank at 510 nm and 700 nm with 1 cm path length disposable cuvettes. Total anthocyanin content was calculated using the equations below.

$$A = (A_{510} - A_{700}) \text{ pH } 1.0 - (A_{510} - A_{700}) \text{ pH } 4.5 \quad \text{Equation (1)}$$

$$C \text{ (mg/L)} = (A \times MW \times DF \times 1000)/(\epsilon \times 1) \quad \text{Equation (2)}$$

Where:
A is the absorbance of the diluted anthocyanin sample;
C is the anthocyanin concentration (mg/L);
MW is the molecular weight (449.2 for cyanidin-3-glucoside);
DF is the dilution factor; and
$\epsilon$ is the molar absorptivity (26900 for cyanidin-3-glucoside).

Figure 2:
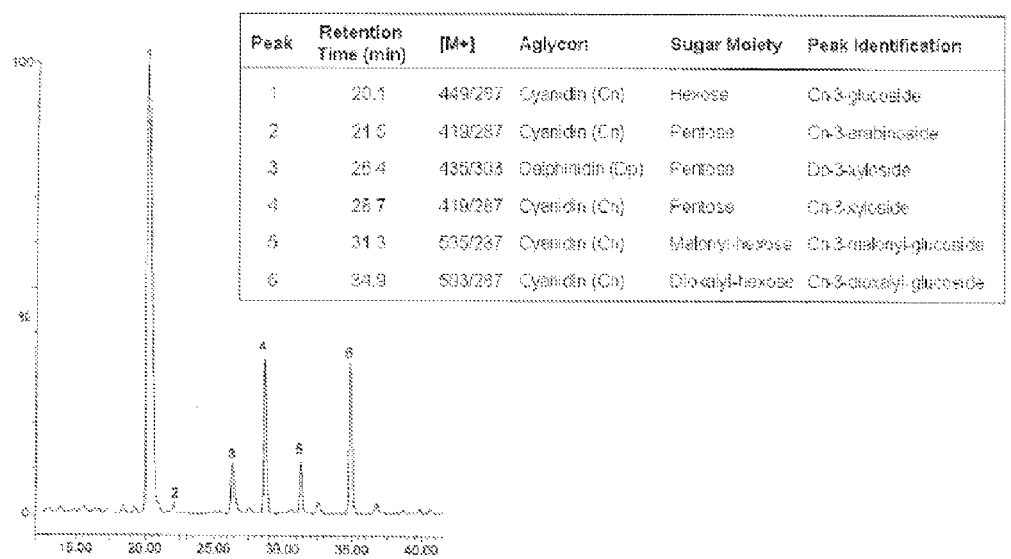
FIG. 2 depicts a standard HPLC chromatogram of a blackberry extract made according to the present invention.

Color density and polymeric color were calculated using absorption at 420, 510 and 700 nm with and without bisulfite treatment. The percentage of polymeric color was determined by the ratio of polymerized color to color density.

ii) Total Phenolic Measurement. Total phenolic content in the berry extract was estimated based on the method of Singleton and Rossi (1965) using gallic acid as a standard. Twenty (20) µL of diluted samples was added to 1.58 mL distilled water along with 100 µL of a 2N Forlin-Ciocalteu phenol reagent. All solutions were mixed thoroughly and then allowed to sit at room temperature for 1 min. Three hundred (300) µl saturated sodium carbonate solution (200 g/L) was then added to each sample. The absorbance was measured at 765 nm with a Beckman UV-visible spectrophotometer after incubation for 2 hr at room temperature. Total phenolics were determined based on the standard curve generated with 0.2, 0.4, 0.6, 0.8, and 1.0 mg/mL of gallic acid.

iii) Trolox Equivalent Antioxidant Capacity (TEAC) Assay. TEAC assay for the berry extract was carried out using a Beckman DU640B spectrophotometer following procedures described by Re et al., (1999). ABTS•+ was produced by reacting 7 mM ABTS with 2.5 mM potassium persulfate for 16 h in the dark at room temperature. The ABTS•+ solution was diluted with ethanol to an absorbance of 0.70 (±0.02) at 734 nm and equilibrated at 30° C. Twenty (20) µl of the berry extract samples were added to 980 nl of diluted ABTS•+ solution, such that each final sample produced between 20-80% inhibition of the blank absorbance. The absorbance readings were taken continuously every 6 s for 6 min at 734 nm at 30° C. Trolox standards in ethanol with final concentration ranging from 0 to 16.8 µM were prepared and assayed under the same conditions. The total antioxidant capacity of the berry extract was calculated and expressed as µmol Trolox equivalent (TE) per gram of dried blackberry extract (DBE). The total antioxidant capacity (TAC) of the berry extract was determined using an improved TEAC assay (Re et al., 1999), which assessed the capacity of a compound or sample to scavenge ABTS•+ in terms of Trolox equivalent. The average TAC value of the berry extract was 66.98±1.27 mmol TE per gram of DBE (see Table 3).

iv) Anthocyanin Composition. HPLC-UV-MS analysis was performed using a X-Bridge™ C18 column (250 mm×4.6 mm, 5 µm) (Waters) equipped with an X-Bridge™ C18 guard column with a Waters 2690 separation module equipped with a 996 photodiode array detector, and coupled on-line with a Waters Micromass ZMD 4000 Mass Spectrometer. The mobile phase consisted of 10% formic acid (A) and 100% acetonitrile (B). The elution conditions were as follows: 0-45 min, linear gradient from 1 to 16% B (v/v); 46-50 min, linear gradient from 16% to 100% B; 51-60 min, 100% B; post-time 5 min with 1% B; flow rate 1 mL/min. The UV-visible detection wavelength was 524 nm and the injection volume was 50 µL of the berry extract. The MS instrument was operated at the following settings: ESP+ mode; capillary voltage, 3.0 kV; cone voltage, 35 V; desolvation temperature, 300° C.; source temperature, 100° C.; scan range, 100-1000 m/z. The HPLC profile of the berry extract showed six major peaks as identified as 1-6 (FIG. 2). Peak identification was carried out based on the molecular weight and structural information obtained from their MS spectra, in addition to their retention times from HPLC-UV-vis spectra.

It is notable that other small peaks as shown in the chromatogram in FIG. 2 were not identifiable by MS and their identity remains unknown. Cyanidin-3-glucoside (peak 1) was the main component (71.0%) in the berry extract with the respective parent and daughter ion pairs (m/z 449/287). The other three major peaks (peak 4, 12.4%; peak 5, 3.5%; peak 6, 11.6%) revealed the m/z values of 419/287, 535/287 and 593/287 which were identified as cyanidin-3-xyloside, cyanidin-3-malonylglucoside and cyanidin-3-dioxalylglucoside respectively, in accordance with data previously reported by Stintzing et al. (2002). Cyanidin-3-arabinoside (peak 2) was also identified, and was in agreement of the initial report by Dugo et al. (2001) using blackberry extracts. Another small peak (peak 3), with the respective parent and daughter ion pairs (m/z 435/303), was detected in the blackberry extract and is being reported for the first time. Based on its retention time, this compound has been tentatively identified as delphinidin-3-xyloside.

EXAMPLE 7

Figure 3:
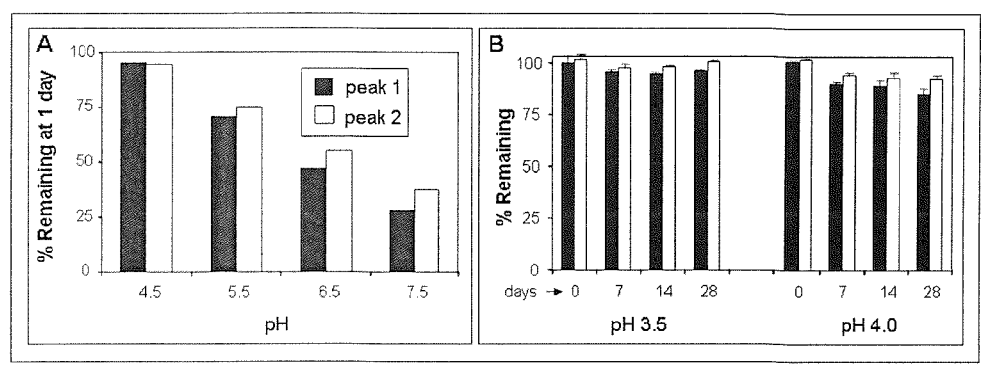
FIGS. 3A and 3B show the stability of anthocyanins as a function of pH and time.

An HPLC assay was used to quantify the anthocyanin content and stability in berry samples. The standard chromatogram gave two peaks corresponding to: peak 1=cyanidin-3-glucoside and cyanidin-3-sambubioside; and peak 2=cyanidin-3-rutinoside and cyanidin-3-(2G-xylosylrutinoside). A standard curve showed excellent linearity over a range of from 50 to 2000 µg/mL with $R^2 > 0.999$ for both peak 1 and peak 2. FIG. 3A depicts the stability of peak 1 and peak 2 after one day at 4° C. in formulations made from pH 4.5 to 7.5. FIG. 3B depicts the stability of peak 1 and peak 2 after 28 days at 4° C. in formulations made at pH 3.5 or pH 4.0.

Freeze-dried berries (prepared as described in Example 2) were formulated at a final concentration of 10% w/w in mixtures having different pHs from pH 7.5, 6.5, 5.5, 4.5, 4.0, and 3.5 and stored at 4° C. for 1 day. As shown in FIG. 3A, peak 1 and peak 2 showed much greater stability at lower pH values after 1 day. The results of a second study are shown in FIG. 3B. In this study, the berries were formulated at pH 3.5 and 4. Formulation of the berries at pH 3.5 provided excellent stability for peak 1 (96.0±0.8%) and peak 2 (100.2±0.4%) over 1 month at 4° C.

EXAMPLE 8

Blackberry extract (19.12 g, see Example 3) was dissolved in 500 mL water to produce a stock solution of 38.24 mg extract/mL. Total anthocyanin content of the 19.12 g blackberry extract was found to be 181.3 mg/L by the pH differential method. This corresponded to a total anthocyanin content of 90.6 mg from the 19.12 g of blackberry extract (0.5% w/w anthocyanins).

Two (2) mL of the blackberry extract, corresponding to 76.48 mg extract was mixed with 8 mL of 10% mannitol and lyophilized to produce a dried berry extract with mannitol. The final mannitol concentration in the solution was 8% and the final pH ranged from 2.5 to 2.6. In addition, blackberry extract alone (without mannitol) was lyophilized to produce a dried berry extract. The lyophilization procedure for both the dried berry extract with mannitol and dried berry extract is shown in Table 4.

TABLE 4

Lyophilization Cycle Used to Prepare Dried Berry Extract and Dried Berry Extract with Mannitol
Steps 1. Freeze to −40° C.
2. Raise temp to −35° C.
3. Once at −35° C., hold for 3 hr
4. Set vacuum to less 150 microns
5. Raise temp to −10° C.
6. Once at −10° C., hold for 15 hr
7. Maintain vacuum of less than 150 microns
8. Raise temp to 0° C.
9. Once at 0° C., hold for 3 hr
10. Raise Temp to 5° C.
11. Once at 5° C., hold for 10 hr
12. Raise temp to 5° C.
13. Once at 10° C., hold for 3.4 hr
14. Raise temp to 20° C.
15. Once at 20° C., hold for 2.5 hr
16. Break vacuum To observe the stability of the blackberry extract in solution alone, and in the presence of 8% mannitol, the extract was stored at 4° C. and 25° C. for 1 month. As shown in Table 5 below, at both temperatures, the presence of 8% mannitol in solution was able to stabilize the retention of four different anthocyanins in solution designated by Peak 1 (Cn-3-glucoside), Peak 2 (Cn-3-arabinoside), Peak 3 (Cn-3-xyloside), and Peak 4 (Cn-3-malonyl-glucoside).

TABLE 5

Retention of Anthocyanins in Berry Extract Solution and Berry Extract with 8% Mannitol Solution Over 1 Month

| | Peak 1 | Peak 2 | Peak 3 | Peak 4 |
|---|---|---|---|---|
| % Retention of Anthocyanin Peak Area after Storage at 4° C. for 1 month | | | | |
| Berry Extract in Solution | 89.7 ± 0.3 | 86.2 ± 13.2 | 90.7 ± 3.1 | 88.0 ± 6.7 |
| Berry Extract with Mannitol | 106.0 ± 1.0 | 138.0 ± 5.9 | 109.5 ± 4.9 | 115.6 ± 10.7 |
| % Retention of Anthocyanin Peak Area after Storage at 25° C. for 1 month | | | | |
| Berry Extract in Solution | 79.2 ± 0.2 | 75.5 ± 10.8 | 81.3 ± 2.4 | 69.6 ± 3.4 |
| Berry Extract with Mannitol | 101.9 ± 0.6 | 96.7 ± 3.4 | 102.0 ± 4.6 | 77.2 ± 24.3 |

Figure 4:
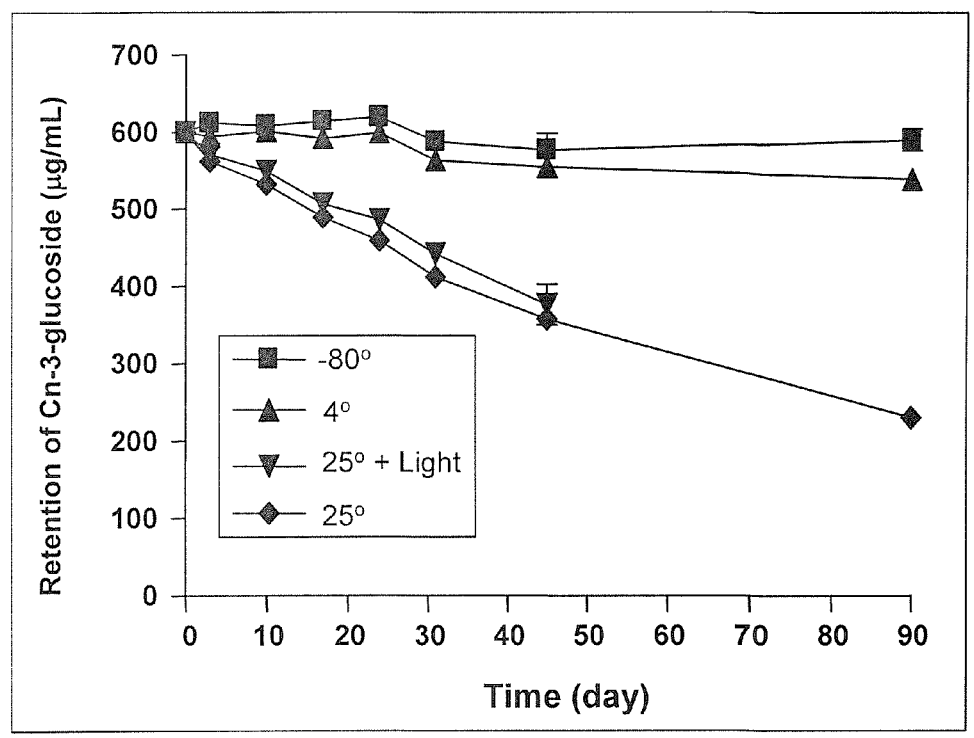
FIG. 4 shows the stability of a specific anthocyanin (cyanidin-3-glucoside) in a blackberry preparation made according to the present invention as a function of time and storage condition.

To observe the stability of blackberry extract in solution stored at four different temperatures or conditions, blackberry extract solution was stored frozen at −80° C. as a control, at 4° C., at 25° C. in the dark, and at 25° C. with light for 90 days. As shown in FIG. 4, the concentration of cyanidin-3-glucoside remained unchanged over 90 days when the blackberry extract solution was stored at −80° C. When the blackberry extract solution was stored at 4° C. over 90 days, there was about a 10% loss in the concentration of cyanidin-3-glucoside. In contrast, there was substantial loss of cyanidin-3-glucoside over 90 days when the blackberry extract solution was stored at 25° C., indicating that the anthocyanin was less stable as the temperature increased.

To further confirm the stability of dried blackberry extracts stored under various conditions and at various temperatures, freeze-dried blackberry powder was stored at −20° C. as a control, dried berry extract was stored at 4° C. and 25° C., and dried berry extract with mannitol stored at 4° C. and 25° C. The stability time points collected were at time 0, 2 weeks, 4 weeks, and 8 weeks.

Sample quantitation was performed by comparing the area of each stability data point to the area for the Time 0 point for each type of sample (freeze-dried blackberry powder, dried extract, or dried extract with mannitol). Equation 3 was used to calculate the concentration (mg/mL) of the sample using the actual weight of sample.

$$C = \text{Sample concentration} = \frac{\text{Actual Weight of Sample}}{\text{Volume of Dilution}} \quad \text{Equation (3)}$$

The percent of each sample peak area relative to the peak area at the Time 0 point was calculated using Equation 4.

$$\% \text{ Peak Area} = \frac{\text{Peak Area at Timepoint}}{\text{Peak Area at Time 0}} \times \frac{C_{Time0}}{C_{Timepoint}} \times 100 \quad \text{Equation (4)}$$

Figure 5:
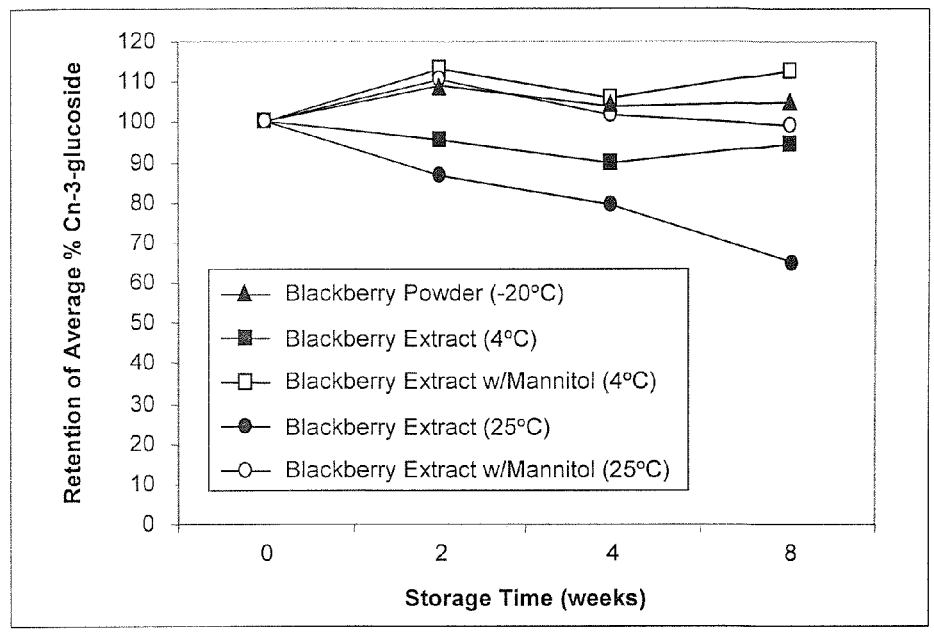
FIGS. 5A and 5B show the stability of anthocyanins in blackberry preparations made according to the present invention as a function of time and temperature.
Figure 5:
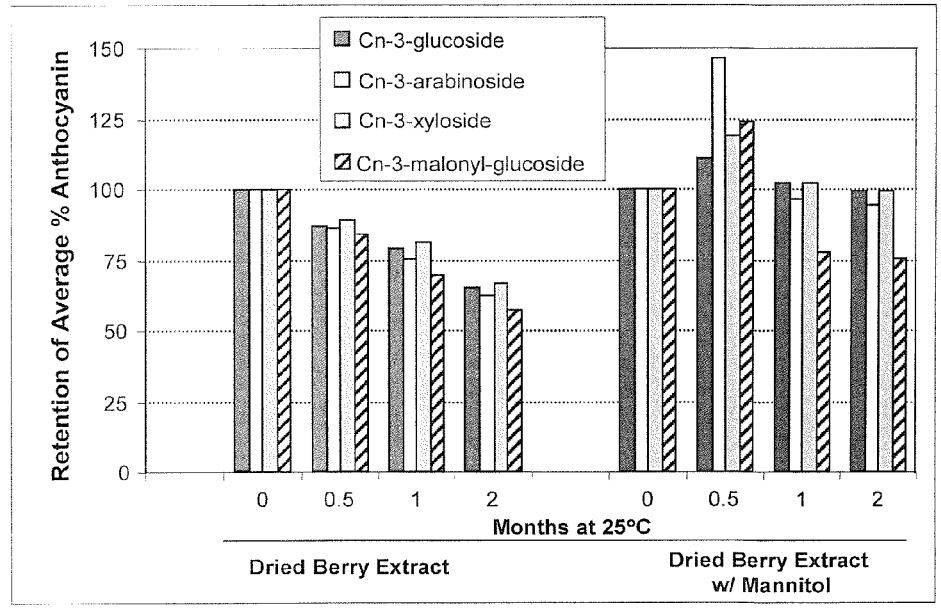

As shown in FIG. 5A, the Cn-3-glucoside in the freeze-dried blackberry powder stored at −20° C. was stable for at least eight weeks. Likewise, Cn-3-glucoside remained stable in both the dried blackberry extract and the dried blackberry extract with mannitol stored for 8 weeks at 4° C. Cn-3-glucoside was continuously lost in the dried blackberry extract over 8 week storage at 25° C. After 8 weeks, the retained Cn-3-glucoside was only about 65% of the original. In contrast, Cn-3-glucoside remained stable in the dried blackberry extract with mannitol stored for 8 weeks at 25° C. Surprisingly, this suggested that mannitol had a stabilizing effect on the dried blackberry extract and in particular Cn-3-glucoside. As shown in FIG. 5B, this effect was also observed for at least three other anthocyanins. FIG. 5B shows the stability of Cn-3-glucoside, Cn-3-arabinoside, Cn-3-xyloside, and Cn-3-malonyl-glucoside over 8 weeks at 25° C. stored as either a dried blackberry extract or dried blackberry extract lyophilized in 8% mannitol.

EXAMPLE 9

A blackberry extract was obtained by extracting 2.5 g blackberry powder (prepared as described in Example 2) three times with ethanol/0.01% HCl (see Example 4). The three extracts were collected and the ethanol was removed by rotoevaporation. Ten (10) mL of water was then used to rehydrate the reddish purple extract. One (1) mL of the blackberry extract was then added to 4 mL of mannitol at a concentration of 10%, 5%, 2%, 1%, or 0%. The blackberry extract/mannitol samples were then lyophilized as described in Example 2. A pink free-flowing powder was only obtained with final mannitol concentration of >8%. The pH of the blackberry extract/mannitol mixture was in the range of pH 2.5 to 2.6. Freeze-drying of the blackberry extract in final mannitol concentrations less than 2% resulted in a sticky gelatin-like product.

EXAMPLE 10

A vanishing lotion base having the composition presented in Table 6 was prepared by heating a water phase to 70° C. An oil phase was heated to about 60° C. and added to the stirring water phase. The resulting mixture was stirred at 70° C. at 1,000 rpm for 30 minutes to produce a homogenous oil-in-water emulsion. After 30 minutes the oil-in-water emulsion was allowed to mix at room temperature at 1,000 rpm for 2 hours. The lotion was q.s. to 100% and a pH of 3.1. The lotion was then allowed to sit at room temperature overnight to cure. To 18 g of the vanishing lotion base, 2 g of blackberry powder (Example 2) was added to produce a final 10% blackberry lotion. The lotion had a purple color that when applied to human skin and rubbed, vanished within 10-15 seconds.

TABLE 6

Composition of Vanishing Lotion Base Used to Prepare a 10% Blackberry Lotion

| Ingredients | Lotion Formula % (w/w) |
|---|---|
| Water | 83.39 |
| Propylene Glycol | 3.33 |
| Sorbitol, 70% | 2.22 |
| Sorbic Acid | 0.22 |
| Butylated Hydroxytoluene | 0.11 |
| Simethicone | 0.11 |
| Sub-total Water Phase | 89.38 |
| Petrolatum | 3.89 |
| Cetostearyl Alcohol | 3.06 |
| Brij 58 | 2.78 |
| Glyceryl Monostearate | 0.22 |
| PEG 400 Monostearate | 0.67 |
| Sub-total Oil Phase | 10.62 |
| Total | 100 |

EXAMPLE 11

The composition described in Example 10 was prepared, except that the blackberry extract described in Example 3 was used. The lotion was prepared identically as described in Example 10 except that to 18 g of the vanishing lotion base (Table 6), 2 g of dried blackberry extract (Example 3) was added to produce a final 10% blackberry extract lotion. The lotion had a purple color that when applied to human skin and rubbed, vanished within 10-15 seconds.

EXAMPLE 12

A 1 kg vanishing cream base was prepared using the formula set forth in Table 7.

TABLE 7

Formula for Preparing Vanishing Cream Base

| Ingredients | % w/w | Calculated weight (g) for 1 kg batch |
|---|---|---|
| Water for injection | 79.8 | 798 |
| Propylene Glycol | 3.0 | 30 |
| Sorbitol, 70% | 2.0 | 20 |
| Sorbic Acid | 0.2 | 2 |
| Butylated Hydroxytoluene | 0.1 | 1 |
| Simethicone | 0.1 | 1 |
| Sub-total water phase | 85.2 | 852 |
| Petrolatum, white | 5.6 | 56 |
| Cetostearyl alcohol | 4.4 | 44 |
| Brij 58 | 4.0 | 40 |

TABLE 7-continued

Formula for Preparing Vanishing Cream Base

| Ingredients | % w/w | Calculated weight (g) for 1 kg batch |
|---|---|---|
| Glyceryl monostearate | 0.2 | 2 |
| PEG-400 monostearate | 0.6 | 6 |
| Sub-total oil phase | 14.8 | 148 |
| TOTAL | 100 | 1000 |

The cream was prepared by first preparing the water phase. Water (798 g) was added to the mixing vessel followed by 30 g propylene glycol. This wax mixed until homogeneous. Next 20 g of 70% sorbitol was added, and then 2 g sorbic acid. This was mixed until homogeneous and then headed to 60-70° C. Butylated hydroxytoluene (1 g) was then added and mixed followed by 1 g simethicone. The water phase was mixed until homogenous at 60-70° C. To prepare the oil phase, the following materials were added to a separate vessel; 56 g white petrolatum, 44 g of cetostearyl alcohol, 40 g of Brij 58, 2 g of glyceryl monostearate, 6 g of polyethylene glycol 400 monostearate. After the addition, the oil phase was heated at 60-70° C. until melted to produce a homogenous phase. Next, the melted oil phase was slowly added to the oil phase and mixed to obtain a homogenous mixture between 60-70° C. The mixture was stirred for an additional 30 min, and then allowed to cool while stirring to 30-35° C. The net weight was adjusted to 1000 g with water and then mixed to produce a homogeneous white placebo cream, pH 3.2. To this cream, freeze-dried blackberry powder (Example 2) was added directly to the placebo cream to produce 1%, 5%, and 10% blackberry cream. Separately, freeze-dried blackberry extract prepared as described in Example 3 was added to produce 1%, 5%, and 10% blackberry extract cream. The pH of all creams was adjusted to pH 3.5 by adding 2N potassium hydroxide. Creams containing either freeze-dried blackberry powder or blackberry extract were pink-red in color depending on the final concentration. All creams applied to human skin and rubbed vanished into the skin with 10-15 seconds after continuous rubbing.

EXAMPLE 13

An enteric-coated blackberry powder capsule was prepared. Empty hard gelatin capsules (#3 Coni-Snap white opaque, Capsugel Lot #589552) having a mean capsule weight of 46.53±0.61 mg were filled with 120 mg of active blackberry powder (Example 2). Fifteen capsules each were enteric-coated with either Coating Solution A or Coating Solution B:
Coating Solution A: 12.50 g EUDRAGIT L-100 and 6.25 g triethyl citrate dissolved in 81.25 g of acetone: isopropyl alcohol (60:40 v/v).
Coating Solution B: 12.50 g EUDRAGIT S-100 and 6.25 g triethyl citrate dissolved in 81.25 g of acetone: isopropyl alcohol (60:40 v/v).

As is known in the art, EUDRAGIT L-100 is soluble above pH 6, whereas EUDRAGIT S-100 is soluble above pH 7. For each coating solution (A and B), 15 individual capsules were coated by taking the capsule fully closed from one end and dipping it in the solution for 2 seconds. About 60% of the capsule was submerged. Residual coating solution was removed by gently touching tip of capsule to a cloth. The solution was evaporated in a stream of airflow from the hood. After 2 hours, the capsule was inverted and the same procedure was repeated. After 2 hours the 15 dry coated capsules were individually weighed and the means were calculated for each coating solution. The average weight of the coating film for each coating solution was calculated, subtracting the average weight of an uncoated capsule from the average weight of the corresponding coated capsule. The average coating weight for capsules coated with coating Solution A and Solution B was 5.53 mg and 4.92 mg, respectively.

A modified version of the disintegration procedure from USP 25 (<701>) was followed using three individual enteric-coated capsules for each coating solution and for each of four disintegration fluids (pH 1, pH 4.5, pH 6 and pH 7.4). One capsule was placed in each of three tubes of the basket in the disintegration apparatus. One liter of each buffer maintained at 37° C.±2° C. during the test was used as the immersion fluid and the disintegration time of capsules was recorded. The end point of the disintegration process was taken to be when the capsule had opened completely and disintegrated except for small fragments of the capsule shell. The results are presented in Table 8.

TABLE 8

Disintegration Time of Blackberry Capsules Enteric-Coated with EUDRAGIT L-100 or EUDRAGIT S-100 as a Function of pH

| Type of Capsule | | pH = 1.0 (0.1M HCl) | pH = 4.5 (10 mM Citric-Citrate Buffer) | pH = 6.0 (10 mM Phosphate Buffer) | pH = 7.4 (10 mM Phosphate Buffer) |
|---|---|---|---|---|---|
| Uncoated | Capsule 1 | <5 min | <5 min | <5 min | <3 min |
|  | Capsule 2 | <5 min | <5 min | <5 min | <3 min |
|  | Capsule 3 | <5 min | <5 min | <5 min | <3 min |
| EUDRAGIT L-100 Coated | Capsule 1 | >1 hour | >1 hour | <25 min | <7 min |
|  | Capsule 2 | >1 hour | >1 hour | <25 min | <7 min |
|  | Capsule 3 | >1 hour | >1 hour | <25 min | <7 min |
| EUDRAGIT S-100 Coated | Capsule 1 | >1 hour | >1 hour | >1 hour | <28 min |
|  | Capsule 2 | >1 hour | >1 hour | >1 hour | <28 min |
|  | Capsule 3 | >1 hour | >1 hour | >1 hour | <28 min |

Note:
For ">1 hour", samples were removed from the vessel intact at 1 hour

Figure 6:
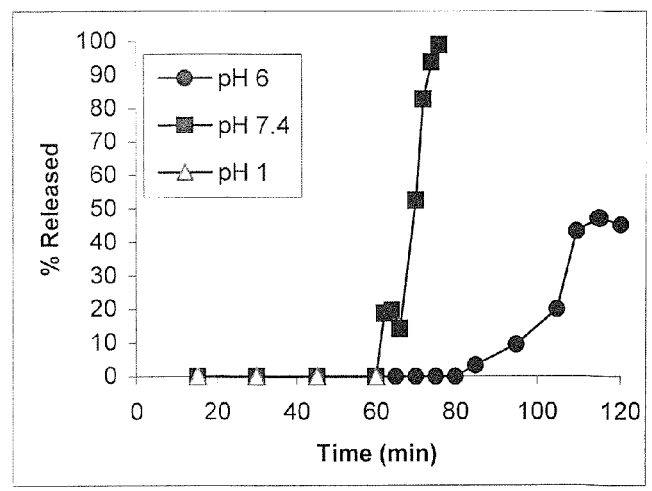
FIG. 6 presents a dissolution profile of enteric-coated hard capsules containing a berry composition according to the present invention.

Next, a simulated dissolution study was completed at 37° C.±2° C. using the blackberry capsule coated with EUDRAGIT L-100 (as noted above, a polymer coating that dissolves at a pH greater than 6). The results are summarized in FIG. 6. Two capsules were placed in medium having pH 1 for 1 hour at 37° C.±2° C., and then transferred intact to medium of either pH 6 or pH 7.4. EUDRAGIT L-100 coated capsules disintegrated very rapidly at pH 7.4 and released their contents. However, the capsules disintegrated more slowly at pH 6 and had released only about 50% of their contents within the first 60 minutes at pH 6.

EXAMPLE 14

Coni-Snap (#2) white opaque capsules from Capsugel were used to prepare enteric-coated capsules comprising blackberry extract with mannitol prepared as described in Example 8. An enteric-coating solution was used to coat the capsules. The coating solution was made by dissolving Eudragit L-100 (12.54 g) in 81.26 g coating solvent containing 6.14 g triethyl citrate. The coating solvent was acetone: isopropyl alcohol (60:40 v/v). Empty uncoated capsules (average weight of 58.6±0.9 mg) were hand-filled with dried blackberry extract with mannitol powder. The average weight of filled capsules was 134.4±15.3 mg. Filled capsules were then enteric-coated with Eudragit L-100 using a Torpac enteric-capsule coater. The coated capsules were allowed to dry.

Figure 7:
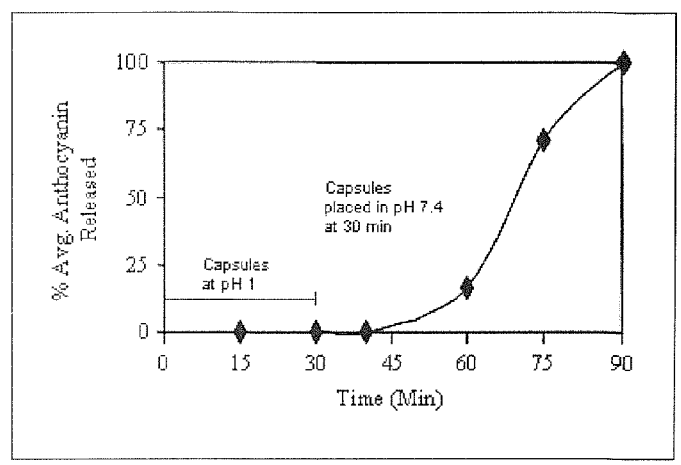
FIG. 7 shows a dissolution profile of enteric-coated hard capsules containing a berry extract according to the present invention.

A two-phase pH dissolution study was performed by first exposing a coated capsule to 30 mL 0.1N HCl, pH 1 at 37° C. for 30 min while stirring at 50 rpm. Two mL samples were removed at 15 min and 30 min to assay for anthocyanin release. After 30 min, the capsule was transferred to 30 mL PBS, pH 7.4 buffer at 37° C. stirring at 50 rpm. Two (2) mL of sample was removed from the PBS after 10, 30, 45 and 60 min. Twenty (20) µl of formic acid (1% final formic acid concentration) was added to each sample to acidify. The volume lost in the vessel each time was replaced with 2 mL of PBS. The results as shown in FIG. 7 demonstrate that anthocyanins were not released from the intact capsule at pH 1 for 30 min. However, after transfer to pH 7.4, the capsules underwent disintegration and anthocyanins were released. Plotted in FIG. 7 is the average anthocyanin released for three capsules.

EXAMPLE 15

A chewing gum base (see Table 9) was prepared by preheating a gum base to 150° F. and a Sigma blade mixer to 120° F. About 40% of Sorbogem712 Crystalline Sorbitol was added to the warmed mixer. The preheated gum base was added to the mixer, followed by an additional 40% of the Sorbogem 712 Crystalline Sorbitol. The liquids were then blended except for the aspartame and spearmint flavor. The liquids were then added to the preheated mixer and the mixer was turned on. The remaining 20% of the Sorbogem712 Crystalline Sorbitol was added.

The entire blend was mixed for 3 minutes and then the aspartame was added. The gum was then mixed an additional 5 minutes and then the spearmint flavor was added. The gum was then mixed for an additional 3 minutes and then blackberry powder (Example 2) was added so that the final blackberry powder was 5% of the total weight. The blackberry gum was mixed an additional 3 minutes and the gum was removed form the mixer. The blackberry gum was sheeted, scored, and cut to predetermined portion sizes.

TABLE 9

Composition of Gum Base Used to Prepare a 10% Blackberry Chewing Gum

| Ingredients | Gum Base % (w/w) |
|---|---|
| SORBOJEM 712 Crystalline Sorbitol | 49.6 |
| PALOGA Gum Base | 25.7 |
| Mannitol | 10.0 |
| MALTISWEET 3145 Maltitol Syrup | 9.7 |
| Glycerin | 3.9 |
| Spearmint Flavor | 1.0 |
| Aspartame | 0.1 |
| Total | 100 |

EXAMPLE 16

A second embodiment of a blackberry chewing gum was prepared. Silicon dioxide, magnesium stearate, sorbitol, and mannitol were obtained from Spectrum. Pharmagum C was purchased from SPI Polyols. Carmine 52% Purple Type Color and Natural Blackberry Flavor were obtained from Wild Flavors. Sugartab was purchased from JRS Pharma.

Compressible chewing gum blends were prepared as shown in Table 10 to determine the needed compression force to form a suitable tablet. The formulation powder was prepared using the target weight of 2000 mg per chewing gum tablet. The following procedures were used to prepare the formulation mixtures. Pharmagum C was placed in the V-blender (Patterson-Kelly Co.) along with the liquid flavor and the mix was allowed to blend for 2 min. To this blend was the first addition of silicon dioxide to adsorb any residual liquid and the mix was allowed to blend for 15 min. A sieve was used to break up any clumps that may have formed during this addition. Dried berry extract with mannitol (Example 7) was removed from the vials, weighed and placed in the V-blender; the mix was allowed to blend for 5 min. Sorbitol was then added and the mix was allowed to blend for 5 min. Powdered color was added if needed and the mix was allowed to blend for 5 min. Magnesium stearate was then added and the mix was allowed to blend for 5 min. Finally, the second addition of silicon dioxide was added and the mix was allowed to blend for 5 min.

Two thousand (2000) mg of a gum formulation were placed in the punch and die set (0.6500", square arc, punch/die, Natoli Engineering). Chewing gum was compressed using a Carver Carver Hydraulic Tablet press (Model C) at compression forces of 2500, 3000, 3500, and 10,000 pounds of pressure. Formulation #16 pressed at 10,000 pounds of pressure was found to be the most desirable chewing gum formulation in terms of hardness and sweetness.

pH of 1.9. This sample was then centrifuged for 10 min at 12,000 g to obtain a final dark-red solution.

HT-29 human colorectal cancer cells (ATCC, HTB38) were grown in McCoy's 5A medium supplemented with 10% fetal bovine serum, 100 IU/mL penicillin, and 10 μg/mL streptomycin and maintained in a humidified atmosphere with 5% $CO_2$ at 37° C. For the cell proliferation assay, HT-29 cells were seeded at a density of $1.2 \times 10^4$ cells/well in 96-well plates and incubated under normal growth conditions overnight to allow cells to attach and proliferate. The berry extract was added in final concentrations ranging from 13.6 to 49.2 μg monomeric anthocyanins/mL medium to each well. Vehicle controls were the normal media with the corresponding pH adjusted using 2.5 N HCl solution of each treated group. At the 0.5, 2, 4 hr time points, the medium was replaced with fresh medium and the cells were cultured for a total of 48 or 72 hr. Cell growth was measured using the MTT assay as previously described (Visconti et al., 1999). Briefly, an MTT stock solution (5 mg/mL) was prepared by dissolving MTT in PBS, pH 7.4. The stock solution was added at 1:10 v/v to the medium in each well, and plates were incubated in the dark at 37° C. for 4 hr. Next, supernatant was removed and 200 μl of 0.04 N HCl in isopropanol was added to each well. After keeping in the dark at room temperature for 1 hr, plates were read at 570 nm using an ELISA plate reader. Cell viability was calculated using Equation 5:

$$\% \text{ inhibition} = (ABS_{Ctrl} - ABS_{St})/ABS_{Ctrl} \times 100\% \qquad \text{Equation (5)}$$

where $ABS_{St}$ is an absorbance of cells treated with the berry extract and $ABS_{Ctrl}$ is the absorbance of corresponding vehicle control.

TABLE 10

Composition (%) of Excipients in the Blackberry Flavored Gum Formulations

|  | Pharmagum | Liquid Flavor | Silicon Dioxide | Sorbitol | Sugartab | Powdered Flavor | Berry Extract w/Mannitol | Color | Magnesium Stearate | Mannitol |
|---|---|---|---|---|---|---|---|---|---|---|
| 1 | 75.0 | 2.0 | 2.0 | 10.0 | 0.0 | 8.0 | 0.0 | 0.5 | 0.5 | 2.0 |
| 2 | 71.0 | 4.0 | 4.0 | 10.0 | 0.0 | 8.0 | 0.0 | 0.5 | 0.5 | 2.0 |
| 3 | 67.0 | 6.0 | 6.0 | 10.0 | 0.0 | 8.0 | 0.0 | 0.5 | 0.5 | 2.0 |
| 4 | 63.0 | 8.0 | 8.0 | 10.0 | 0.0 | 8.0 | 0.0 | 0.5 | 0.5 | 2.0 |
| 5 | 71.0 | 4.0 | 4.0 | 12.0 | 0.0 | 6.0 | 0.0 | 0.5 | 0.5 | 2.0 |
| 6 | 73.0 | 4.0 | 2.0 | 12.0 | 0.0 | 6.0 | 0.0 | 0.5 | 0.5 | 2.0 |
| 7 | 69.0 | 6.0 | 4.0 | 0.0 | 12.0 | 6.0 | 0.0 | 0.5 | 0.5 | 2.0 |
| 8 | 73.0 | 4.0 | 2.0 | 0.0 | 12.0 | 6.0 | 0.0 | 0.5 | 0.5 | 2.0 |
| 9 | 70.0 | 5.0 | 3.0 | 0.0 | 8.0 | 0.0 | 0.0 | 0.5 | 1.0 | 12.5 |
| 10 | 69.0 | 5.0 | 3.0 | 0.0 | 8.0 | 0.0 | 0.0 | 0.5 | 2.0 | 12.5 |
| 11 | 69.0 | 6.0 | 3.0 | 0.0 | 8.0 | 0.0 | 12.5 | 0.5 | 1.0 | 0.0 |
| 12 | 68.0 | 7.0 | 3.0 | 0.0 | 7.0 | 0.0 | 12.5 | 0.5 | 1.0 | 0.0 |
| 13 | 69.0 | 5.0 | 3.0 | 0.0 | 8.0 | 0.0 | 12.5 | 0.5 | 2.0 | 0.0 |
| 14 | 68.0 | 7.0 | 3.0 | 0.0 | 7.0 | 1.0 | 12.5 | 0.5 | 1.0 | 0.0 |
| 15 | 69.0 | 5.0 | 3.0 | 0.0 | 8.0 | 0.0 | 12.5 | 0.5 | 2.0 | 0.0 |
| 16 | 69.0 | 5.0 | 3.0 | 0.0 | 8.0 | 0.0 | 12.5 | 0.5 | 2.0 | 0.0 |

EXAMPLE 17

To evaluate health and medical benefits, and in particular anti-proliferative/anti-cancer effects, of the composition of the present invention, a blackberry extract was obtained as described in Example 4 by extracting 2.5 g blackberry powder (prepared as described in Example 2) three times with 20 mL of ethanol/0.01% HCl under sonication. The three samples were collected, combined, and centrifuged for 10 min at 12,000 g. The supernatant was then filtered to collect dark red solution. Ethanol was then removed at 40° C. using a rotary evaporator to obtain a dark red, viscous liquid. Ten (10) mL of water was added to produce a dark-red suspension having a There are numerous reports on the growth inhibition of cancer cells in vitro by various anthocyanin-containing extracts or purified anthocyanin fractions from various kinds of fruits and vegetables (Olsson et al., 2004; Seeram et al., 2004; Zhao et al., 2004; Reddy et al., 2005; Yi et al., 2005; Zhang et al., 2005). Among them, Olsson et al. showed an average inhibition of 53% on HT29 cells at the highest concentration of strawberry extracts (Olsson et al., 2006). Yi et al. found that the $IC_{50}$ for blueberry extracts with HT29 cells ranged from 1000-3000 μg/mL (Yi et al., 2005). Commercially prepared grape, bilberry, and chokeberry anthocyanin-rich extracts (AREs) were investigated by Zhao et al. and it was demonstrated that all of the three extracts inhibited HT29 cell growth, with chokeberry ARE being the most potent inhibitor (Zhao et al., 2004). In addition, Parry et al. reported similar results with black raspberry, cranberry, and chardonnay grape seed flour extracts on the anti-proliferative effects on HT29 cells (Parry et al., 2006). However, for all of these studies mentioned above, the HT29 cells were treated with extracts for at least 24 hr. In addition, to our knowledge, the present study is the first to investigate the growth inhibition effect of an aqueous extract from blackberries on the proliferation of HT29 cells. Moreover, in the present studies, cells were treated with a reduced contact time of 0.5 to 4 hr instead of the typical 24 hr. It was found that the berry extract inhibited the growth of HT-29 cells in a concentration-dependent manner. In addition, the inhibition rates of HT-29 cells versus anthocyanin concentration were comparable in these studies to extracts derived from other fruits.

Figure 8:
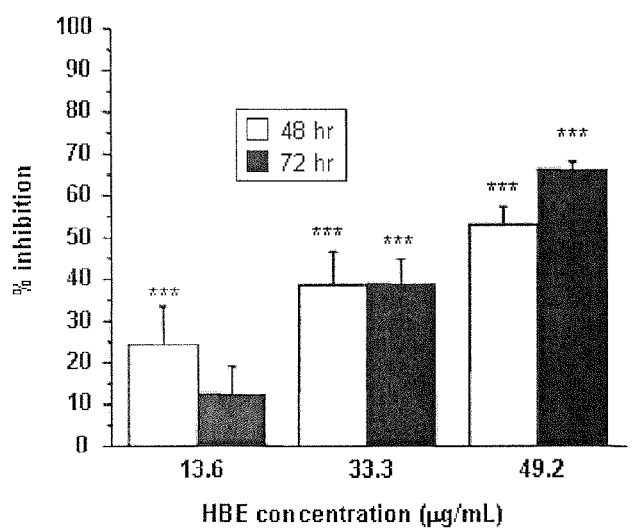
FIG. 8 shows inhibition of proliferation of HT-29 cells by a blackberry extract according to the present invention.

As shown in FIG. 8, HT-29 cells were exposed to berry extract for 2 hr and then incubated with fresh media for 48 or 72 hr. The growth of HT-29 cells was inhibited by 24% to 53% ($P<0.001$) at concentrations ranging from 13.6 to 49.2 μg monomeric anthocyanins/mL medium at 48 hr At the 72 hr time point, although the HT-29 cell growth inhibition was not significant ($P=0.2$) at the concentration of 13.6 μg monomeric anthocyanins/mL medium, significant inhibition of 39% and 66% ($P<0.001$) was observed at higher concentrations of 32.8 and 49.2 μg monomeric anthocyanins/mL medium, respectively. The studies by Malik et al. (2003) and Zhao et al. (2004) using anthocyanin-rich berry extracts suggested that the increase in inhibition with exposure time (24, 48 and 72 hr) was mainly due to growth of control cells over time as there was little or no change in the growth of cells exposed to the berry extracts. In contrast, in the present studies, cells were exposed to berry extract for a fixed period of time and then removed and replaced with fresh media for addition incubation for 48 or 72 hr. As a consequence, a trend of increasing inhibition over time was not observed in the present studies. For example, the percentage inhibition of 38.6% and 38.99% were not statistically different at the 48 and 72 hr time point after two hour exposure of a concentration of 32.8 monomeric anthocyanins/mL medium, respectively. Similar growth inhibition rates and patterns were also observed at 48 and 72 hr time point after 0.5 hr and 4 hr exposure of the berry extract (data not shown) which may indicate that the active components (including anthocyanins) that lead to inhibition by the berry extract may be rapidly taken up by the cells.

EXAMPLE 18

The experiment described in Example 17 was repeated, with the exception that media containing berry extract was added to the HT-29 cells after incubation for 0.5 hr at 37° C., rather than adding berry extract directly to the cells. The results showed a similar inhibition rate at all concentrations as the berry extract with a concentration of 13.6 μg monomeric anthocyanins/mL medium was added directly to cells. Since anthocyanins are known to be less stable at neutral pH than low pH, this result may suggest that there are other active components in the berry extract. However, this aspect was beyond the scope of the present studies and remains an active area of investigation.

There are a few studies that have been performed to elucidate the mechanism behind the chemoprevention effects of anthocyanins or anthocyanin-rich extracts on cancer cells. Hibiscus (Chang et al., 2005), Lingonberry (Wang et al., 2005), and bilberry (Katsube et al., 2003) anthocyanins-rich extract were found inhibiting the growth of HL60 (human leukemia cells) through the induction of apoptosis. Hou et al. showed anthocyanins inhibit tumorigenesis induced by TPA on mouse JB6 (+) cells by blocking activation of the MAPK pathway (Hou et al., 2004). Several groups have reported that anthocyanins could suppress the cyclooxygenase activity, which may also play a key role on carcinogenesis (Wang et al., 1999; Seeram et al., 2001; Hou et al., 2005). Hakimuddin et al. found that the inhibition of MCF-7 cell proliferation by a flavonoid fraction from a red wine was related to its inhibition of calcium and calmodulin-promoted phosphodiesterase activity (Hakimuddin et al., 2004). The molecular mechanism by which the berry extract inhibits the growth of various cancer cells is currently being investigated.

It will be appreciated that other known agents having anti-proliferative or anti-cancer properties may be combined with the present composition to enhance its anti-proliferative/anti-cancer activity, including, but not limited to: alkylating agents such as cisplatin, nitrosoureas such as carmustine, antimetabolites such as 5-fluoruracil, methotrexate, anthracyclines such as daunorubicin and doxorubicin, topoisomerase II inhibitors such as topotecan, and mitotoic inhibitors such as taxanes (paclitaxel, docetaxel) and the vinca alkaloids (vinblastine, vincristine, and vinorelbine). In addition, combinations with antibodies are also envisioned such as trastuzumab, imatinib, gefitinib, erlotinib, rituximab, and bevacizumab.

EXAMPLE 19

To evaluate the anti-inflammatory effects of the blackberry extract of the present invention, bone marrow cells were obtained by flushing the femurs of BALB/c mice (Harlan Sprague-Dawley Laboratories, Indianapolis, Ind.) with 1×HBSS. Cells were cultured in 100 mm bacteriological petri dishes at $2 \times 10^5$ cells/mL in 10 mL of complete RPMI 1640 medium (supplemented with 10% heat-inactivated fetal calf serum, 1 mM HEPES, 2 $_c$M L-glutamine, 10 U/mL penicillin, 100 U/mL streptomycin, 50 $_c$M 2-mercaptoethanol) containing 20-25 ng/mL GM-CSF at 37° C., 7% $CO_2$. The cells were supplemented with an additional 10 mL of complete RPMI 1640 with 20-25 ng/mL GM-CSF on day 3. On day 6, 10 mL of supernatant was removed from each plate and spun down. The cells were resuspended in fresh 10 mL of complete RPMI 1640 with 20-25 ng/mL GM-CSF and added back to the Petri dishes. Non-adherent to lightly adherent cells were harvested on day 7 as dendritic cells (DCs) and used for the in vitro studies. For the interleukin-12 (IL-12) release assay, day 7 harvested bone marrow derived dendritic cells (BMDDCs) were plated in 200 cl of complete RPMI 1640 containing 20-25 ng/mL GM-CSF at $4 \times 10^5$ cells/well in 48-well tissue culture plates (Costar) at 37° C., 7% $CO_2$ overnight. The media was removed and replaced with fresh complete RPMI 1640.

Figure 9:
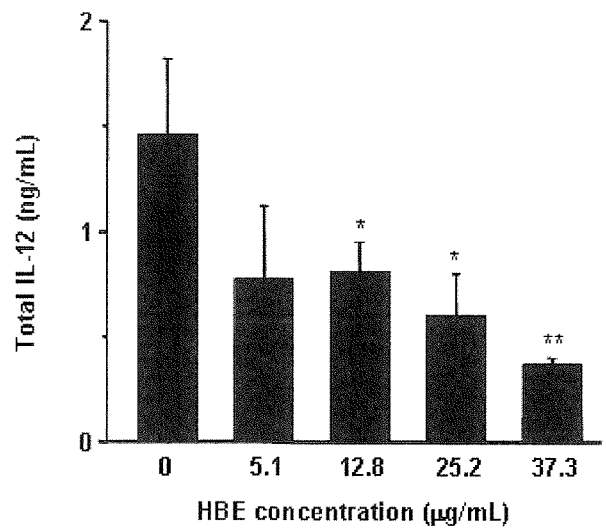
FIG. 9 shows inhibition of IL-12 release from murine dendritic cells by a blackberry extract according to the present invention.
Figure 9:
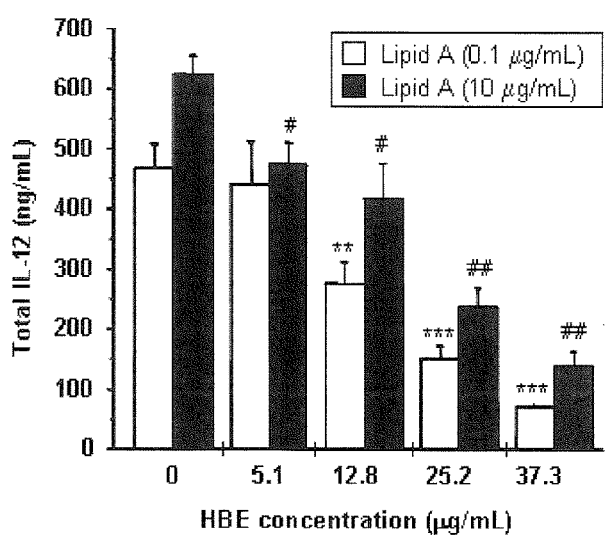

Blackberry extract prepared as described in Example 3 was then added in concentrations providing from 5.1 to 37.3 μg monomeric anthocyanins/mL media and plates were incubated for 30 min. High-dose (10 μg/mL) or low-dose (0.1 μg/mL) Lipid A from *Salmonella Minnesota* R595 (Re) (List Biological Laboratories, Campbell, Calif.) was then added to each well with or without the berry extract treatment. After 24 hr, supernatant in each well was collected and stored at −80° C. until IL-12 measurement. Total IL-12 concentration in supernatant was measured using a murine total IL-12 ELISA Kit (Pierce) according to the instructions from the manufacturer. Results are presented in FIG. 9.

Previous studies by Pergola and colleagues demonstrated that part of the anti-inflammatory activity of a specific blackberry extract was due to the suppression of nitric oxide (NO)

production in J774 cells by cyanidin-3-O-glucoside (Pergola et al., 2006). Rossi et al. (2003) showed that the anthocyanin fraction from blackberry extract exerted multiple protective effects in carrageenan-induced pleurisy in rats. Nevertheless, most of the in vitro studies utilizing anthocyanin-containing extracts from other fruits or vegetables have focused on the effect of the extracts on NO synthesis and TNF-α levels in vitro using activated macrophages (Wang and Mazza, 2002a; Wang and Mazza, 2002b; Hou et al., 2005). Other studies have assessed the effects of extracts on the inflammation induced by hydrogen peroxide and TNF-a in human microvascular endothelial cells (Youdim et al., 2002). To our knowledge, there have been few or no studies assessing the anti-inflammatory effects of anthocyanin-containing extracts on dendritic cells. DCs are potent antigen-presenting cells and function as initiators and modulators of the immune response. Lipid A is known to induce maturation of DCs resulting in synthesis of high levels of pro-inflammatory IL-12 that enhances both innate (natural killer cell) and acquired (B and T cells) immunity.

As shown in FIG. 9A, baseline release of IL-12 from non-stimulated DCs was low, with an IL-12 concentration of only 1.46 ng/mL. However, for all concentrations of the berry extract added, the IL-12 release was reduced in a concentration dependent manner with only 0.37 ng IL-12/mL secreted using a concentration of 37.3 μg monomeric anthocyanins/mL medium. As expected, both high-dose (10 μg/mL) and low-dose (0.1 μg/mL) lipid A resulted in very high release of IL-12 from DCs of 624 ng/mL and 468 ng/mL, respectively (FIG. 9B). In the low dose lipid A treatment group, the concentration of IL-12 in cell culture supernatant was decreased in a concentration dependent manner from 468 to 72 ng/mL when the berry extract was added in the range from 5.1 to 37.3 $_c$g monomeric anthocyanin/mL. A similar pattern was observed in the high-dose lipid A treatment group, with the reduction of IL-12 release ranging from 474 to 138 ng/mL when the berry extract was added in the range from 5.1 to 37.3 μg monomeric anthocyanin/mL. Thus, the berry extract significantly inhibited the release of IL-12 from murine BMD-DCs with or without Lipid A treatment. These results suggest that the berry extracts of the present invention may have significant anti-inflammatory properties, mediated at least in part by reduced production of certain inflammatory cytokines.

EXAMPLE 20

To evaluate the ability of various cryoprotectants to stabilize anthocyanins in berry extracts, a blackberry extract was prepared from blackberry puree (Example 1) with the extraction method described in Example 3. The cryoprotectants evaluated were:
1. Dextran: Sigma, 6 kD, Cat#9004-54-0, Lot#1288265;
2. Polyvinyl pyrrolidone (PVP): Sigma, 10 kD, Cat#9003-39-8, Lot#108K0157;
3. Carboxymethyl cellulose (CMC): Sigma, 90 kD, Cat#419273, Lot# MKBF8492V;
4. Polyethylene glycol (PEG): Sigma, 8 kD, Cat#89510, Lot#1394369;
5. Lactose: Spectrum, Cas#63-42-3, Lot#V00335;
6. Sucrose: Fisher, Cat# BP220-1, Lot#037621;
7. Trehalose: Sigma, Cat# TO167, Lot#020M70073V; and
8. Hydroxyethyl starch (HES): Sigma, Cat#H6382, Lot#093H0405V, MW>1 million.

The experimental groups evaluated were: 1) extract powder; 2) cryoprotectant-extract (2:1, w/w) powder; and 3) cryoprotectant-extract (8:1, w/w) powder groups.

A 10% aqueous solution of each cryoprotectant was prepared. For the carboxymethyl cellulose, a 5% aqueous solution was prepared. A stock blackberry extract solution was prepared (140 mg extract powder/mL). A mixture of 10% (v/v) cryoprotectant solution (5% for carboxymethyl cellulose) in blackberry extract stock solution (140 mg/mL) was prepared to provide a final cryoprotectant powder:extract powder ratio (w/w) of 2:1 and 8:1.

To evaluate anthocyanin stability over time, 10 mL samples (1 mL/sample×3 repetitions×3 time points=9 mL) of each solution were prepared for each of the above cryoprotectants. The final concentrations of extract in each extract-cryoprotectant solutions were 36.82 mg/mL and 11.48 mg/mL for cryoprotectant:berry extract ratios (w/w) of 2:1 and 8:1, respectively.

Next, stability of anthocyanins during storage at ambient temperature was evaluated according to the following procedure:

1. One (1) mL aliquots of extract-cryoprotectant or extract solution (without cryoprotectant) were freeze-dried and the freeze-dried powder were stored at room temperature (22-28) in 20 ml glass scintillation vials sealed with white polypropylene screw caps (Fisher, cat# 03-341-25E).
2. Total Anthocyanin content (TA) was determined using a pH differential method [37.1.68 AOAC Official Method 2005.02, J. AOAC Int. 88, pg 1269 (2005), incorporated herein by reference in its entirety] at days 0, 14, and 28.
3. A total of 18 samples were evaluated for each cryoprotectant [3 time points 2 concentrations 3 repetitions (n=3)=18 samples].

Total samples tested at each time point=2 concentrations of cryoprotectant 8 samples 3 repetitions (n=3)+3 repetition of pure extract=51.

Total samples in this experiment=51×3 time points=153.
4. Retention of TA at day 14 and 28 was calculated as percentage of the TA of each corresponding cryoprotectant or pure extract group as measured at day 0.

The results are presented in Tables 11-19 below.

TABLE 11

Retention of TA over time at 22-28° C.
for berry extract powder without cryoprotectant.

| Extract Alone | Day 0 | Day 14 | Day 28 |
|---|---|---|---|
| | 100.00 ± 6.86 | 88.04 ± 2.20 | 84.15 ± 4.03 |

TABLE 12

Retention of TA over time at 22-28° C.
for berry extract-Trehalose powder.

| Trehalose:Extract (w/w) | Day 0 | Day 14 | Day 28 |
|---|---|---|---|
| 2:1 | 100.00 ± 8.21 | 103.59 ± 6.56 | 107.76 ± 3.44 |
| 8:1 | 100.00 ± 10.47 | 105.12 ± 2.51 | 99.26 ± 9.10 |

TABLE 13

Retention of TA over time at 22-28° C. for berry extract-Lactose powder.

| Lactose:Extract (w/w) | Day 0 | Day 14 | Day 28 |
|---|---|---|---|
| 2:1 | 100.00 ± 5.82 | 101.45 ± 4.34 | 99.37 ± 2.36 |
| 8:1 | 100.00 ± 6.72 | 101.82 ± 5.94 | 100.59 ± 3.47 |

TABLE 14

Retention of TA over time at 22-28° C. for berry extract-Sucrose powder.

| Sucrose:Extract (w/w) | Day 0 | Day 14 | Day 28 |
|---|---|---|---|
| 2:1 | 100.00 ± 5.21 | 96.28 ± 1.12 | 99.37 ± 2.36 |
| 8:1 | 100.00 ± 5.97 | 101.93 ± 3.63 | 101.55 ± 1.90 |

TABLE 15

Retention of TA over time at 22-28° C. for berry extract-Dextran powder.

| Dextran:Extract (w/w) | Day 0 | Day 14 | Day 28 |
|---|---|---|---|
| 2:1 | 100.00 ± 6.45 | 97.97 ± 8.24 | 101.70 ± 12.41 |
| 8:1 | 100.00 ± 7.51 | 100.58 ± 8.15 | 100.93 ± 5.61 |

TABLE 16

Retention of TA over time at 22-28° C. for berry extract-PVP powder.

| PVP:Extract (w/w) | Day 0 | Day 14 | Day 28 |
|---|---|---|---|
| 2:1 | 100.00 ± 9.52 | 91.36 ± 0.35 | 86.73 ± 4.35 |
| 8:1 | 100.00 ± 7.69 | 101.10 ± 7.13 | 100.69 ± 7.82 |

TABLE 17

Retention of TA over time at 22-28° C. for berry extract-HES Powder.

| HES:Extract (w/w) | Day 0 | Day 14 | Day 28 |
|---|---|---|---|
| 2:1 | 100.00 ± 3.36 | 96.93 ± 3.21 | 91.98 ± 1.70 |
| 8:1 | 100.00 ± 6.72 | 103.83 ± 4.83 | 93.82 ± 7.76 |

TABLE 18

Retention of TA over time at 22-28° C. for berry extract-PEG powder.

| PEG8000:Extract (w/w) | Day 0 | Day 14 | Day 28 |
|---|---|---|---|
| 2:1 | 100.00 ± 7.61 | 97.12 ± 11.64 | 80.36 ± 3.24 |
| 8:1 | 100.00 ± 10.19 | 75.87 ± 5.36 | 63.95 ± 3.93 |

TABLE 19

Retention of TA over time at 22-28° C. for berry extract-CMC powder.

| CMC:Extract (w/w) | Day 0 | Day 14 | Day 28 |
|---|---|---|---|
| 2:1 | 100.00 ± 5.74 | 99.12 ± 10.09 | 102.63 ± 5.14 |
| 8:1 | 100.00 ± 6.86 | 92.15 ± 7.13 | 92.58 ± 13.69 |

As clearly demonstrated in Tables 11-19, with the exception of PEG increased retention of Total Anthocyanin content, i.e., improved anthocyanin stability, was observed in all berry extract-cryoprotectant powder compositions tested as compared to berry extract powder without cryoprotectant.

It will therefore be appreciated that the present invention provides a simple, convenient method for preparing a berry extract having a stabilized anthocyanin content, for use in compositions providing health and medical benefits to individuals consuming them. The foregoing description of the preferred embodiment of this invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

Citations of Literature

Castro B C, Kresty L A, Kraly C L, Pearl D K, Knobloch T J, Schut H A, Stoner G D, Mallery S R, Weghorst C M. Chemoprevention of oral cancer by black raspberries. Anticancer Res 22: 4005-4016 (2002).

Chang Y C, Huang H P, Hsu J D, Yang S F, and Wang C J. Hibiscus anthocyanins rich extract-induced apoptotic cell death in human promyelocytic leukemia cells. Toxicol Appl Pharmacol 2005, 205:201-212.

Dugo P, Mondello L, Errante G, Zappia G, and Dugo G. Identification of anthocyanins in berries by narrow-bore high-performance liquid chromatography with electrospray ionization detection. J Agric Food Chem. 2001, 49(8):3987-3992.

Giusti M M, and Wrolstad R E. Characterization and measurement of anthocyanins by UV-visible spectroscopy. In Current Protocols in Food Analytical Chemistry; R. E. Wrolstad; T. E. Acree; H. An; E. A. Decker; M. H. Penner; D. S. Reid; S. J. Schwartz; C. F. Shoemaker and P. Sporns, Eds.; John Wiley & Sons: NY, 2001; pp F1.2.1-F1.2.13.

Hakimuddin F, Paliyath G, and Meckling K. Selective cytotoxicity of a red grape wine flavonoid fraction against MCF-7 cells. Breast Cancer Res Treat 2004, 85, 65-79.

Hecht S S, Huang C, Stoner G D, Li J, Kenney P M J, Sturla S J, Carmella S G. Identification of cyanidin glycosides as constituents of freeze-dried black raspberries which inhibit anti-benzo[α]pyrene-7,8-diol-9,10-epoxide induced NFκB and AP-1 activity. In Press: Carcinogenesis.

Hertog, M G L et al. Intake of potentially anticarcinogenic flavonoids and their determinants in adults in the Netherlands. Nutr. Cancer. 20:21-29, 1993.

Hou D X, Yanagita T, Uto T, Masuzaki S, and Fujii M. Anthocyanidins inhibit cyclooxygenase-2 expression in LPS-evoked macrophages: Structure-activity relationship and molecular mechanisms involved. Biochem Pharmacol. 2005, 70(3):417-425.

Hu C, Zawistowski J, Ling W, Kitts D D. Black Rice (*Oryza sativa* L. Indica) Pigmented Fraction Suppresses both Reactive Oxygen Species and Nitric Oxide in Chemical and Biological Model Systems. J Agric Food Chem 51: 5271-5277 (2003).

Huang C, Huang Y, Li J, Hu W, Aziz R, Tang M-S, Sun N, Cassady J, Stoner G D. Inhibition of Benzo[α]pyrene Diol- Epoxide-induced Transactivation of Activated Protein 1 and Nuclear Factor ĸB by Black Raspberry Extracts. Cancer Res 62: 6857-6863 (2002).

Katsube N, Iwashita K, Tsushida T, Yamaki K, Kobori M. Induction of apoptosis in cancer cells by Bilberry (*Vaccinium myrtillus*) and the anthocyanins. J Agric Food Chem 51: 68-75 (2003).

Kresty A, Morse M A, Morgan C, Carlton P S, Lu J, Gupta A, Blackwood M, Stoner G D. Chemoprevention of esophageal tumorigenesis by dietary administration of lyophilized black raspberries. Cancer Res 61: 6112-6119 (2001).

Liu M, Li X Q, Weber C, Lee C Y, Brown J, Liu R H. Antioxidant and antiproliferative activities of raspberries. J Agric Food Chem 50: 2926-2930 (2002).

Malik M, Zhao C, Schoene N, Guisti M M, Moyer M P, and Magnuson B. A. Anthocyanin-rich extract from *Aronia meloncarpa* E induces a cell cycle block in colon cancer but not normal colonic cells. Nutr Cancer. 2003, 46(2):186-196.

Macheix, J J, Fleuriet A. and Billot J. Fruit Phenolics. CRC Press: Boca Raton, Fla. 1990.

Morais H, Ramos C, Forgacs E. Cserhati T, Oliviera J. Influence of storage conditions on the stability of monomeric anthocyanins studied by reversed-phase high-performance liquid chromatography. J Chromatogr B Analyt Technol Biomed Life Sci. 770 (1-2):297-301, 2002.

Nielsen I L, Haren G R, Magnussen E L, Dragsted L O, Rasmussen S E. Quantification of anthocyanins in commercial black currant juices by simple high-performance liquid chromatography. Investigation of their pH stability and antioxidative potency. J Agric Food Chem. 51(20): 5861-6, 2003.

Olsson M E, Gustaysson K E, Andersson S, Nilsson A, and Duan R D. Inhibition of cancer cell proliferation in vitro by fruit and berry extracts and correlations with antioxidant levels. J Agric Food Chem. 2004, 52(24): 7264-7271.

Olsson M E, Andersson C S, Oredsson S, Berglund R H, and Gustaysson K E. Antioxidant levels and inhibition of cancer cell proliferation in vitro by extracts from organically and conventionally cultivated strawberries. J Agric Food Chem 2006, 54, 1248-1255.

Parry J, Su L, Moore J, Cheng Z, Luther M, Rao J N, Wang J Y, and Yu L L. Chemical compositions, antioxidant capacities, and antiproliferative activities of selected fruit seed flours. J Agric Food Chem 2006, 54, 3773-3778.

Pergola C, Rossi A, Dugo P, Cuzzocrea S, and Sautebin L. Inhibition of nitric oxide biosynthesis by anthocyanin fraction of blackberry extract. Nitric Oxide. 2006, 15(1):30-39.

Proteggente A R, Pannala A S, Paganga G, Van Buren L, Wagner E, Wiseman S, Van De Put F, Dacombe C, Rice-Evans C A. The antioxidant activity of regularly consumed fruit and vegetables reflects their phenolic and vitamin C composition. Free Radic Res. 36:217-33, 2002.

Re R, Pellegrini N, Proteggente A, Pannala A, Yang M, and Rice-Evans C. Antioxidant activity applying an improved ABTS radical cation decolorization assay. Free Radic Biol Med. 1999, 26, 1231-1237.

Reddy M K, Alexander-Lindo R L, and Nair M G. Relative inhibition of lipid peroxidation, cyclooxygenase enzymes, and human tumor cell proliferation by natural food colors. J Agric Food Chem 2005, 53, 9268-9273.

Rice-Evans C A, Miller N J, Bolwell P G, Bramley P M, Pridham J B. The relative antioxidant activities of plant-derived polyphenolic flavonoids. Free Radic Res. 22:375-83, 1995.

Rodrigo K A, Rawal Y, Renner R J, Schwartz S J, Tian Q, Larsen P E, Mallery S R. Suppression of the tumorigenic phenotype in squamous cell carcinoma cells by an ethanol extract derived from freeze-dried black raspberries. In Press: Nutrition and Cancer.

Rossi A, Serraino I, Dugo P, Di Paola R, Mondello L, Genovese T, Morabito D, Dugo G, Sautebin L, Caputi A P, and Cuzzocrea S. Protective effects of anthocyanins from blackberry in a rat model of acute lung inflammation. Free Radic Res. 2003, 37(8): 891-900.

Rubinskiene M, Jasutiene I, Venskutonis P R, Viskelis P. HPLC determination of the composition and stability of blackcurrant anthocyanins. J Chromatogr Sci. 43(9):478-82, 2005.

Sellappan S, Akoh C C, and Krewer G. Phenolic Compounds and Antioxidant Capacity of Georgia-Grown Blueberries and Blackberries. J. Agric. Food. Chem. 50:2432-2438, 2002.

Seeram N P, Adams L S, Hardy M L, and Heber D. Total cranberry extract versus its phytochemical constituents: antiproliferative and synergistic effects against human tumor cell lines. J Agric Food Chem. 2004, 52(9):2512-2517.

Seeram N P, Momin R A, Nair M G, and Bourquin L D. Cyclooxygenase inhibitory and antioxidant cyanidin glycosides in cherries and berries. Phytomedicine 2001, 8, 362-369.

Singleton V, and Rossi J. Colorimetry of total phenolics with phosphomolybdic-phosphotungstic acid reagents. Am. J. Enol. Vitic. 1965, 16, 144-158.

Stintzing F C, Stintzing A S, Carle R, and Wrolstad R E. A novel zwitterionic anthocyanin from evergreen blackberry (*Rubus laciniatus* Willd.). J Agric Food Chem. 2002, 50(2): 396-399.

Tsao R, and Yang R. Optimization of a new mobile phase to know the complex and real polyphenolic composition: towards a total phenolic index using high-performance liquid chromatography. Journal of Chromatography A 1018:29-40, 2003.

Visconti A, Minervini F, Lucivero G, and Gambatesa V. Cytotoxic and immunotoxic effects of *Fusarium* mycotoxins using a rapid colorimetric bioassay. Mycopathologia 1991, 113, 181-186.

Wang H, et al. Oxygen radical absorbing capacity of anthocyanins. J Agric Food Chem. 47:304-9, 1997.

Wang H, Nair M G, Strasburg G M, Chang Y C, Booren A M, Gray J I, and DeWitt D L. Antioxidant and antiinflammatory activities of anthocyanins and their aglycon, cyanidin, from tart cherries. J Nat. Prod. 162:802, 1999.

Wang S Y, Feng R, Bowman L, Penhallegon R, Ding M, and Lu Y. Antioxidant activity in lingonberries (*Vaccinium vitis-idaea* L.) and its inhibitory effect on activator protein-1, nuclear factor-kappaB, and mitogen-activated protein kinases activation. J Agric Food Chem 2005, 53, 3156-3166.

Wang J and Mazza G. Effects of anthocyanins and other phenolic compounds on the production of tumor necrosis factor alpha in LPS/IFN-gamma-activated RAW 264.7 macrophages. J Agric Food Chem. 2002a, 50(15): 4183-4189.

Wang J and Mazza G. Inhibitory effects of anthocyanins and other phenolic compounds on nitric oxide production in LPS/IFN-gamma-activated RAW 264.7 macrophages. J Agric Food Chem. 2002b, 50(4): 850-857.

Xue H, Aziz R M, Sun N, Cassady J M, Kamedulis L M, Xu Y, Stoner G D, and Klaunig J E, Inhibition of cellular transformation by berry extracts. Carcinogenesis 22: 351-356 (2001).

Yi W, Fischer J, and Akoh C C. Study of anticancer activities of muscadine grape phenolics in vitro. J Agric Food Chem. 2005, 53, 8804-8812.

Youdim K A, McDonald J, Kalt W, and Joseph J A. Potential role of dietary flavonoids in reducing microvascular endothelium vulnerability to oxidative and inflammatory insults. J Nutr Biochem. 2002, 13(5):282-288.

Zhang Y, Vareed S K, and Nair M G. Human tumor cell growth inhibition by nontoxic anthocyanidins, the pigments in fruits and vegetables. Life Sci 2005, 76, 1465-1472

Zhao C, Giusti M M, Malik M, Moyer M P, and Magnuson B A. Effects of commercial anthocyanin-rich extracts on colonic cancer and nontumorigenic colonic cell growth. J Agric Food Chem. 2004, 52(20): 6122-6128.

What is claimed is:

1. A stabilized anthocyanin-containing berry powder having antioxidant and anti-inflammatory activity, prepared by the steps of: i) physically disrupting a quantity of anthocyanin-containing berries; ii) exposing the physically disrupted berries to an acidic solvent composition having a pH of from about 1 to about 3 to provide an acidic extract of berries; iii) adding a cryoprotectant in an amount of at lease 2:1 (w/w) cryoprotectant: anthocynanin-containing berry extract to provide a stabilized anthocyanin-containing berry extract; and iv) forming the stabilized anthocyanin-containing berry extract into a berry powder.

2. The composition of claim 1, wherein the cryoprotectant is selected from the group consisting of a monosaccharide, a disaccharide, a polysaccharide, a polymer, and combinations thereof.

3. The composition of claim 2, wherein the cryoprotectant is selected from the group consisting of glucose, fructose, maltose, ribose, mannose, xylose, trehalose, sucrose, myo-inositol, phosphorylated inositols, glycerol, hydroxyethyl starch, dextran, hyaluronic acid, polyvinylpyrrolidone, alginates, carrageenan, cyclodextrins, polyvinyl alcohol, carboxymethyl cellulose, methyl cellulose, hydroxypropyl cellulose, hydroxypropylmethyl cellulose, xanthan gum, chitosan, and combinations thereof.

4. The composition of claim 1, wherein the anthocyanin-containing berry extract is derived from a blackberry.

5. The composition of claim 1, further comprising recovering an anthocyanin-containing berry extract having a pH of from about 1.0 to about 4.5.

6. The composition of claim 1, wherein the anthocyanin-containing berry extract is brought to a pH of about 3.5.

7. The composition of claim 1, wherein the solvent composition comprises an alcohol and at least one acid.

8. The composition of claim 7, wherein the alcohol is a lower alcohol.

9. The composition of claim 8, wherein the lower alcohol is selected from the group consisting of methanol, ethanol, propanol, butanol, and combinations thereof.

10. The composition of claim 7, wherein the at least one acid is selected from the group consisting of hydrochloric acid, acetic acid, citric acid, lactic acid, trifluoroacetic acid, aspartic acid, glutamic acid, a sulfur-containing acid, sulfonic acid, formic acid, phosphoric acid, maleic acid, and combinations thereof.

11. The composition of claim 1, wherein the physically disrupted anthocyanin-containing berries are dewatered to a water content of up to 20% (w/v) prior to or after exposing to the solvent composition.

12. The composition of claim 1, wherein the anthocyanin-containing berry extract is provided as a formulation adapted for oral administration.

13. The composition of claim 12, wherein the anthocyanin-containing berry extract is provided as a nutritional supplement, a capsule, an enteric-coated capsule, a film-coated capsule, a tablet, an enteric-coated tablet, a film-coated tablet, or a chewing gum.

14. The composition of claim 13, comprising the anthocyanin-containing berry extract in an amount of from about 3% (w/w) to about 90% (w/w).

15. The composition of claim 1, wherein the anthocyanin-containing berry extract is provided as a formulation adapted for topical administration.

16. The composition of claim 15, wherein the anthocyanin-containing berry extract is provided as a lotion, a cream, a mucoadhesive gel, a vanishing lotion, or a vanishing cream.

17. The composition of claim 16, comprising the anthocyanin-containing berry extract in an amount of from about 1% (w/w) to about 20% (w/w).

18. A composition for treating inflammation, oxidative damage, or cancer in a mammal in need thereof, comprising a therapeutically effective amount of a composition as recited in claim 1 in a pharmaceutically acceptable vehicle.

19. A method for preparing a stabilized anthocyanin-containing berry powder having antioxidant and anti-inflammatory activity, comprising:
   physically disrupting a quantity of anthocyanin-containing berries;
   exposing the disrupted berries to an acidic solvent composition having a pH of from about 1 to about 3;
   adding a cryoprotectant in an amount of at least 2:1 (w/w) cryoprotectant: anthocyanin-containing berry extract; and
   forming the stabilized anthocyanin-containing berry extract into a berry powder having a stabilized anthocyanin content.

20. The composition of claim 19, including selecting the cryoprotectant from the group consisting of a monosaccharide, a disaccharide, a polysaccharide, a polymer, and combinations thereof.

21. The method of claim 20, including selecting the cryoprotectant from the group consisting of glucose, fructose, maltose, ribose, mannose, xylose, trehalose, sucrose, myo-inositol, phosphorylated inositols, glycerol, hydroxyethyl starch, dextran, hyaluronic acid, polyvinylpyrrolidone, alginates, carrageenan, cyclodextrins, polyvinyl alcohol, cellulose-derivatives, carboxymethyl cellulose, methyl cellulose, hydroxypropyl cellulose, hydroxypropylmethyl cellulose, xanthan gum, chitosan, and combinations thereof.

22. The method of claim 19, wherein the anthocyanin-containing berry is a blackberry.

23. The method of claim 19, including the step of exposing the physically disrupted anthocyanin-containing berries to the solvent composition and recovering an anthocyanin-containing berry extract having a pH of from about 1.0 to about 4.5.

24. The method of claim 23, including recovering an anthocyanin-containing berry extract having a pH of about 3.5.

25. The method of claim 23, including exposing the physically disrupted anthocyanin-containing berries to a solvent composition comprising an alcohol and at least one acid.

26. The method of claim 25, including exposing the physically disrupted anthocyanin-containing berries to a solvent composition comprising a lower alcohol and at least one acid.

27. The method of claim 26, including selecting the lower alcohol from the group consisting of methanol, ethanol, propanol, butanol, and combinations thereof.

28. The method of claim 26, including selecting the at least one acid from the group consisting of hydrochloric acid, acetic acid, citric acid, lactic acid, trifluoroacetic acid, aspartic acid, glutamic acid, a sulfur-containing acid, sulfonic acid, formic acid, phosphoric acid, maleic acid, and combinations thereof.

29. The method of claim 23, further including the step of dewatering the physically disrupted anthocyanin-containing berries to a water content of up to 20% (w/v) prior to or after the step of exposing to the solvent composition.

* * * * *

UNITED STATES PATENT AND TRADEMARK OFFICE
CERTIFICATE OF CORRECTION

PATENT NO. : 8,367,126 B2
APPLICATION NO. : 13/157531
DATED : February 5, 2013
INVENTOR(S) : Mumper et al.

Page 1 of 1

It is certified that error appears in the above-identified patent and that said Letters Patent is hereby corrected as shown below:

In the Claims

Column 31, line 29, please replace "lease" with --least--.

Signed and Sealed this
Eleventh Day of June, 2013

Teresa Stanek Rea
*Acting Director of the United States Patent and Trademark Office*